(12) United States Patent
Manero et al.

(10) Patent No.: US 6,491,989 B1
(45) Date of Patent: Dec. 10, 2002

(54) FLUORINATED NAPHTHALENE DERIVATIVES AND THEIR USE IN LIQUID CRYSTAL MIXTURES

(75) Inventors: Javier Manero, Liederbach (DE); Wolfgang Schmidt, Köln (DE); Barbara Hornung, Hasselroth (DE)

(73) Assignee: Aventis Reseach & Technologies GmbH & Co. KG, Frankfurt am Main (DE)

( * ) Notice: Subject to any disclaimer, the term of this patent is extended or adjusted under 35 U.S.C. 154(b) by 0 days.

(21) Appl. No.: 09/530,552

(22) PCT Filed: Nov. 3, 1998

(86) PCT No.: PCT/EP98/06938

§ 371 (c)(1), (2), (4) Date: Jul. 10, 2000

(87) PCT Pub. No.: WO99/23074

PCT Pub. Date: May 14, 1999

(30) Foreign Application Priority Data

Nov. 3, 1997 (DE) .......................... 197 48 440
Nov. 3, 1997 (DE) .......................... 197 48 438
Nov. 3, 1997 (DE) .......................... 197 48 435
Nov. 3, 1997 (DE) .......................... 197 48 432

(51) Int. Cl.$^7$ ..................... C09K 19/32; C09K 19/34; C07D 239/02; C07D 213/02; C07D 211/84; C07C 25/12; C07C 43/225

(52) U.S. Cl. ............. 428/1.1; 252/299.61; 252/299.62; 544/303; 544/334; 544/335; 546/339; 546/346; 570/183; 570/187; 570/188

(58) Field of Search .................. 252/299.62; 428/1.1; 544/303, 334, 335; 546/339, 346; 570/183, 188, 187

(56) References Cited

U.S. PATENT DOCUMENTS

| 5,234,950 | A | * | 8/1993 | Edwards et al. | |
| 5,538,988 | A | | 7/1996 | Martinez et al. | 514/384 |
| 6,159,392 | A | * | 12/2000 | Schdmit et al. | 252/299.62 |
| 6,159,561 | A | * | 12/2000 | Schmidt et al. | 428/1.1 |

FOREIGN PATENT DOCUMENTS

| DE | A 19522145 | 12/1995 |
| DE | A 195 22 152 | 12/1995 |
| DE | A 195 22 167 | 12/1995 |
| DE | A 195 22 195 | 12/1995 |
| EP | 0032362 | 8/1984 |
| EP | A 0375404 | 8/1990 |

* cited by examiner

Primary Examiner—Shean C. Wu
(74) Attorney, Agent, or Firm—Frommer Lawrence & Haug LLP

(57) ABSTRACT

Fluorinated naphthalene derivatives of the formula (I)

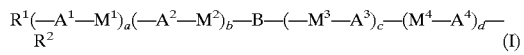

where
B is

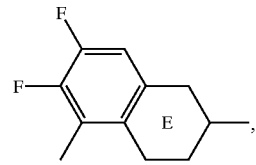

having the meaning

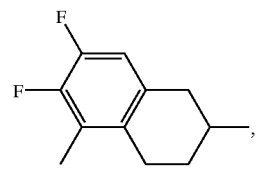

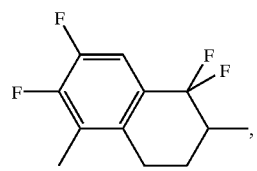
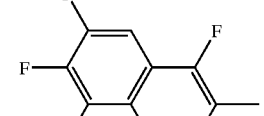

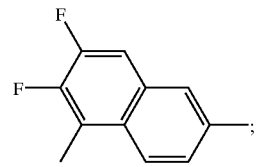

and
$R^1(-A^1-M^1)_a(-A^2-M^2)$ and $(-M^3-A^3)(M^4-A^4)$ $R^2$ are mesogenic radicals, are suitable as components of liquid-crystal mixtures, in particular ferroelectric liquid-crystal mixtures.

9 Claims, No Drawings

FLUORINATED NAPHTHALENE DERIVATIVES AND THEIR USE IN LIQUID CRYSTAL MIXTURES

CROSS-REFERENCE TO RELATED APPLICATION

This application was filed pursuant to 35 U.S.C. 371 from international application no. PCT/EP98/06938, filed Mar. 11, 1998, which in turn claims priority to German Application Nos. 197 48 432.8, 197 48 440.9, 197 48 438.7 and 19748 435.2, all filed Nov. 3, 1997.

BACKGROUND OF THE INVENTION

Field of the Invention

In addition to nematic and cholesteric liquid crystals, chiral tilted smectic (ferroelectric) liquid crystals have also been used recently in commercial display devices.

BACKGROUND OF THE INVENTION

Clark and Lagerwall have been able to show that the use of ferroelectric liquid crystals (FLCs) in very thin cells results in opto-electrical switching or display elements which have response times which are faster by a factor of up to 1000 compared with conventional TN ("twisted nematic") cells (see, for example, EP-A 0 032 362). On the basis of this and other favorable properties, for example the possibility of bistable switching and the fact that the viewing angle is virtually independent of the contrast, FLCs are fundamentally highly suitable for areas of application such as computer displays.

The use of FLCs in electro-optical or fully optical components requires either compounds which form tilted or orthogonal smectic phases and are themselves optically active, or the induction of ferroelectric smectic phases by doping compounds which, although forming such smectic phases, are not themselves optically active, with optically active compounds. The desired phase should be stable over the broadest possible temperature range.

In order to achieve good contrast in electro-optical components, a uniform planar alignment of the liquid crystals is necessary. Good alignment in the $S_A$ and $S_C$ phase can be achieved, for example, if the phase sequence of the liquid-crystal mixture is, with decreasing temperature:

isotropic→N*→$S_A$→$S^*_C$

The prerequisite is that the pitch of the helix in the N* phase is very large (greater than 10 μm) or, even better, is fully compensated (see, for example, T. Matsumoto et al, Proc. of the 6th Int. Display Research Conf., Japan Display, Sep. 30–Oct. 2, 1986, Tokyo, Japan, pp. 468–470; M. Murakami et al., ibid. pp. 344–347). This is achieved by mixing the chiral liquid-crystal mixture having, for example, a left-handed helix in the N* phase with one or more optically active dopants which induce a right-handed helix, in such amounts that the helix is compensated.

Use of Clark and Lagerwall's SSFLCD (surface-stabilized ferroelectric liquid-crystal display) effect for uniform, planar alignment furthermore requires that the pitch in the smectic C* phase is significantly greater than the thickness of the display element (Mol. Cryst. Liq. Cryst. 1983, 94, 213 and 1984, 114, 151).

The optical response time τ [μs] of ferroelectric liquid-crystal systems, which should be as short as possible, depends on the rotational viscosity of the system γ [mPas], the spontaneous polarization $P_s$ [nC/cm²] and the electric field strength E [V/m], in accordance with the equation

$$\tau \sim \frac{\gamma}{P_s \cdot E}$$

Since the field strength E is determined by the electrode separation in the electro-optical component and by the applied voltage, the ferroelectric display medium must have low viscosity and high spontaneous polarization in order to achieve a short response time.

Finally, in addition to thermal, chemical and photochemical stability, a low optical anisotropy Δn and a low positive or preferably negative dielectric anisotropy Δε are required (see, for example, S. T. Lagerwall et al., "Ferroelectric Liquid Crystals for Displays", SID Symposium, October Meeting 1985, San Diego, Calif., USA).

The totality of these requirements can only be achieved by means of mixtures of a plurality of components. The base (or matrix) used preferably comprises compounds which if possible themselves already have the desired phase sequence I→N→$S_A$→$S_C$. Further components of the mixture are frequently added in order to lower the melting point and to broaden the $S_C$ and usually also the N phase, to induce optical activity, for pitch compensation and to match the optical and dielectric anisotropies; however, the rotational viscosity, for example, should if possible not be increased.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B. I. Ostrovski in Advances in Liquid Crystal Research and Applications, Oxford/Budapest, 1980, 469 ff., and the PSFLCD effect is described in DE-A 39 20 625 and EP-A 0 405 346. In contrast to the SSFLCD effect, utilization of these effects requires a liquid-crystalline material having a short $S_C$ pitch.

3,4-Difluorotetralin derivatives for use in liquid-crystal mixtures are disclosed, for example, in DE-A 19522145. Tetrafluorotetralin derivatives for use in liquid-crystal mixtures are disclosed, for example, in DE-A 19522152. Trifluoronaphthalene derivatives for use in liquid-crystal mixtures are disclosed, for example, in DE-A 19522195. Difluoronaphthalene derivatives for use in liquid-crystal mixtures are disclosed, for example, in DE-A 19522167.

However, since the development, in particular of ferroelectric liquid-crystal mixtures, can in no way be regarded as complete, the manufacturers of displays are interested in a very wide variety of components for mixtures. Another reason for this is that only the interaction of the liquid-crystalline mixtures with the individual components of the display device or of the cells (for example the alignment layer) allows conclusions to be drawn on the quality of the liquid-crystalline mixtures too.

BRIEF SUMMARY OF THE INVENTION

The object of the present invention was therefore to provide novel compounds which, in liquid-crystalline mixtures, are suitable for improving the property profile of these mixtures.

Surprisingly, it has been found that fluorinated naphthalene derivatives of the formula (I) are particularly suitable for use in liquid-crystal mixtures. These are, in particular, 6,7difluoro-1,2,3,4-tetrahydronaphthalene derivatives, 1,1, 6,7-tetrafluoro-1,2,3,4-tetrahydronaphthalene derivatives, 1,6,7-trifluoronaphthalene derivatives and 2,3-difluoronaphthalene derivatives of the formula (I).

DETAILED DESCRIPTION OF THE INVENTION 6,7-Difluoro-3,4-dihydro-2H-naphthalen-1-one is disclosed, for example, in Synth. Commun. 1991, 21, 981–7, but there is no mention therein of this molecule or its derivatives being suitable as part of a component of liquid-crystal mixtures.

The invention therefore relates to fluorinated naphthalene derivatives of the formula (I)

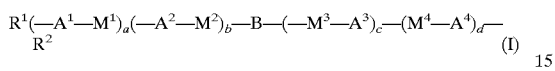

where the symbols and indices are defined as follows:
group B is

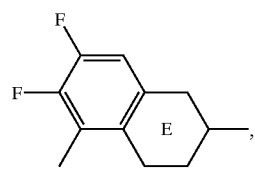

having the meaning

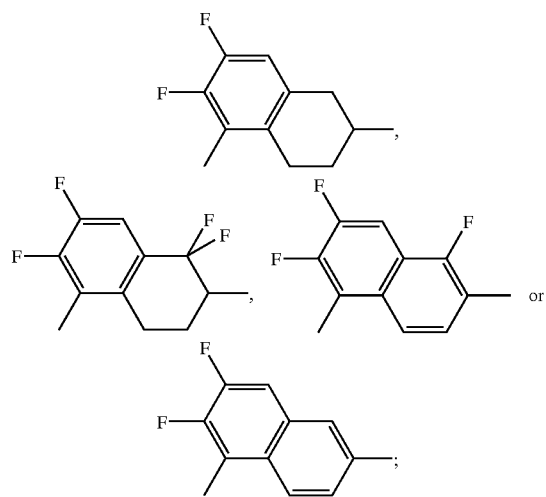

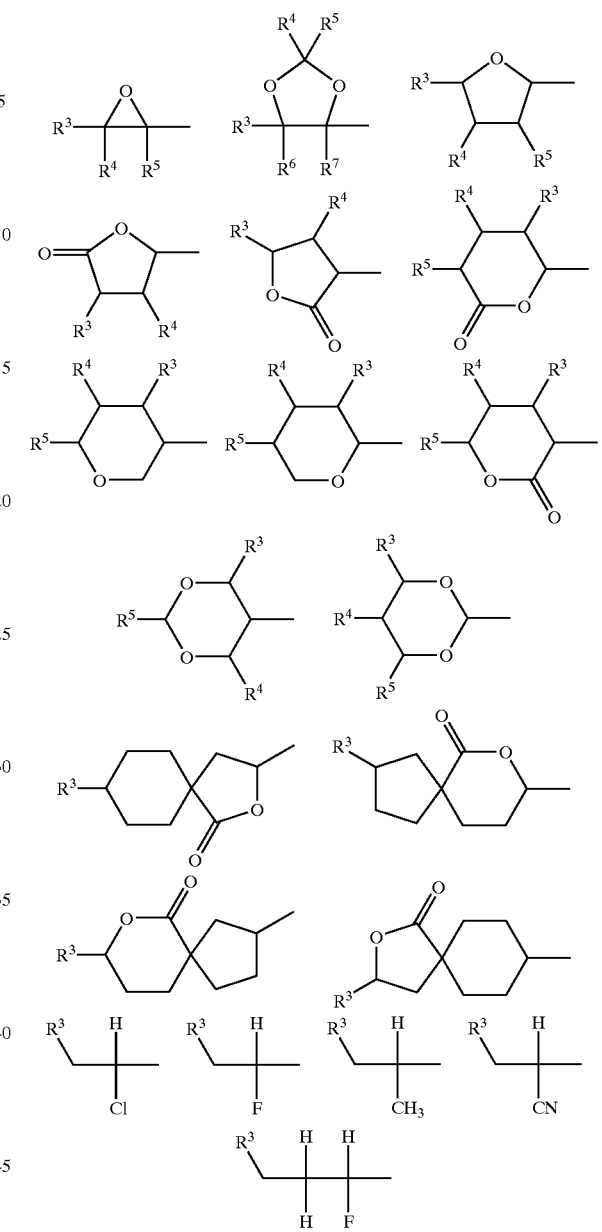

$R^1$ and $R^2$ are identical or different and are
  a) hydrogen, —$OCF_3$, —$CF_3$, —CN, —F, —Cl, —$OCHF_2$, —$OCH_2F$, —$CHF_2$ or —$CH_2F$
  b) a straight-chain or branched alkyl radical (with or without an asymmetrical carbon atom) having 1 to 20 carbon atoms, where
    b1) one or more non-adjacent and non-terminal —$CH_2$— groups may be replaced by —O—, —S—, —CO—O—, —O—CO—, —O—CO—O— or —Si($CH_3$)$_2$—, and/or
    b2) one or more —$CH_2$— groups may be replaced by —CH=CH—, —C≡C—, cyclopropane-1,2-diyl, 1,4-phenylene, 1,4-cyclohexylene or 1,3-cyclopentylene, and/or
    b3) one or more H atoms may be replaced by F and/or Cl, and/or
    b4) the terminal —$CH_3$ group may be replaced by one of the following chiral groups (optically active or racemic):

with the proviso that at most one of the radicals $R^1$ and $R^2$ is hydrogen, —$OCF_3$, —$CF_3$, —CN, —F, —Cl, —$OCHF_2$, —$OCH_2F$, —$CHF_2$ or —$CH_2F$;

$R^3$, $R^4$, $R^5$, $R^6$ and $R^7$ are identical or different and are
  a) hydrogen
  b) a straight-chain or branched alkyl radical (with or without an asymmetrical carbon atom) having 1 to 16 carbon atoms, where
    b1) one or more non-adjacent and non-terminal —$CH_2$— groups may be replaced by —O—, and/or
    b2) one or two —$CH_2$— groups may be replaced by —CH=CH—,
  c) $R^4$ and $R^5$ together may alternatively be —($CH_2$)$_4$— or —($CH_2$)$_5$— if they are bonded to an oxirane, dioxolane, tetrahydrofuran, tetrahydropyran, butyrolactone or valerolactone system;

$M^1$, $M^2$, $M^3$ and $M^4$ are identical or different and are —CO—O—, —O—CO—, —CO—S—, —S—CO—, —CS—O—, —CS—S—, —O—CS—, —S—CS—, —CH₂O—, —O—CH₂—, —CH₂—S—, —S—CH₂—, —CH=CH—, —C≡C—, —CH₂—CH₂—CO—O—, —O—CO—CH₂—CH₂— or a single bond;

A¹, A², A³ and A⁴ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, 1,4-cyclohexylene, in which one or two H atoms may be replaced by CN and/or CH₃ and/or F, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5-diyl, in which one or two H atoms may be replaced by F, Cl and/or CN, naphthalene-2,6-diyl, in which one or more H atoms may be replaced by F, Cl and/or CN, or 1-alkyl-1-silacyclohexane-1,4-diyl;

a, b, c and d are 0 or 1; with the proviso that the compound of the formula (I) does not contain more than four, preferably at least two, five- or multi-membered ring systems.

The provision of compounds of the formula (I) very generally considerably broadens the range of liquid-crystalline substances which are suitable, from various applicational points of view, for the preparation of liquid-crystalline mixtures.

In this connection, the compounds of the formula (I) have a broad range of applications. Depending on the choice of substituents, they can be used as base materials of which liquid-crystalline phases are predominantly composed; however it is also possible to add compounds of the formula (I) to liquid-crystalline base materials from other classes of compound in order, for example, to modify the dielectric and/or optical anisotropy of a dielectric of this type and/or to optimize its threshold voltage and/or its viscosity.

The compounds of the formula (I) are particularly suitable, even when added in small amounts, for influencing the dielectric anisotropy (Δε) toward more highly negative values.

The compounds of the formula (I) according to the invention are particularly suitable for use in nematic and smectic liquid-crystal mixtures, in the case of nematic mixtures in particular for active matrix displays (AM-LCDs) (see, for example, C. Prince, Seminar Lecture Notes, Volume I, p. M-3/3-M-22, SID International Symposium 1997, B. B. Bahadur, Liquid Crystal Applications and Uses, Vol. 1, p. 410, World Scientific Publishing, 1990, E. Lüder, Recent Progress of AM LCD's, Proceedings of the 15$^{th}$ International Display Research Conference, 1995, p. 9–12) and in-plane switching displays (IPS-LCDs), in the case of smectic liquid-crystal mixtures for ECB displays (electrically controlled birefringence), for electroclinic displays and chiral tilted smectic (ferroelectric) displays. The compounds of the formula (I) according to the invention are particularly suitable for use in FLC mixtures for ferroelectric switching and/or display devices which are operated in inverse mode.

The symbols and indices in the formula (I) preferably have the following meanings:

$R^1$ and $R^2$ are preferably identical or different and are
a) hydrogen,
b) a straight-chain or branched alkyl radical (with or without an asymmetrical carbon atom) having 1 to 18 carbon atoms, where
  b1) one or more non-adjacent and non-terminal —CH₂— groups may be replaced by —O—, —CO—O—, —O—CO—, —O—CO—O— or —Si(CH₃)₂—, and/or
  b2) one —CH₂— group may be replaced by cyclopropane-1,2-diyl, 1,4-phenylene or trans-1,4-cyclohexylene, and/or
  b3) one or more H atoms may be replaced by F, and/or
  b4) the terminal CH₃ group may be replaced by one of the following chiral groups (optically active or racemic):

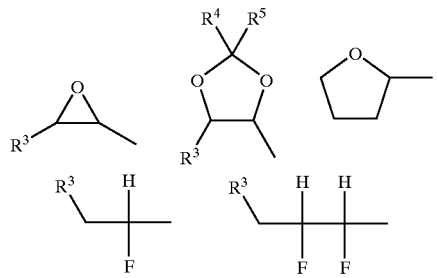

with the proviso that at most one of the radicals $R^1$ and $R^2$ is hydrogen.

$R^1$ and $R^2$ are particularly preferably identical or different and are
a) hydrogen,
b) a straight-chain or branched alkyl radical (with or without an asymmetrical carbon atom) having 1 to 16 carbon atoms, where
  b1) one or two non-adjacent and non-terminal —CH₂— groups may be replaced by —O—, —CO—O—, —O—CO—, —O—CO—O— or —Si(CH₃)₂—, and/or
  b2) one —CH₂— group may be replaced by 1,4-phenylene or trans-1,4-cyclohexylene, and/or
  b3) one or more H atoms may be replaced by F, and/or
  b4) the terminal CH₃ group may be replaced by one of the following chiral groups (optically active or racemic):

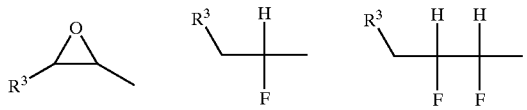

with the proviso that at most one of the radicals $R^1$ and $R^2$ is hydrogen.

$R^3$, $R^4$, $R^5$, $R^6$ and $R^7$ are preferably identical or different and are
a) hydrogen
b) a straight-chain or branched alkyl radical (with or without an asymmetrical carbon atom) having 1 to 14 carbon atoms, where
  b1) one or two non-adjacent and non-terminal —CH₂— groups may be replaced by —O—, and/or
  b2) one —CH₂— group may be replaced by —CH=CH—, c) $R^4$ and $R^5$ together may alternatively be —$(CH_2)_4$— or —$(CH_2)_5$— if they are bonded to an oxirane, dioxolane, tetrahydrofuran, tetrahydropyran, butyrolactone or valerolactone system.

$R^3$, $R^4$, $R^5$, $R^6$ and $R^7$ are particularly preferably identical or different and are a) hydrogen b) a straight-chain or branched alkyl radical (with or without an asymmetrical carbon atom) having 1 to 14 carbon atoms, where b1) one non-terminal —$CH_2$— group may be replaced by —O—, c) $R^4$ and $R^5$ together may alternatively be —$(CH_2)_4$— or —$(CH_2)_5$— if they are bonded to an oxirane, dioxolane, tetrahydrofuran, tetrahydropyran, butyrolactone or valerolactone system.

$M^1$, $M^2$, $M^3$ and $M^4$ are preferably identical or different and are —CO—O—, —O—CO—, —$CH_2$—O—, —O—$CH_2$—, —CH=CH—, —C≡C—, —$CH_2$—$CH_2$—CO—O—, —O—CO—$CH_2$—$CH_2$— or a single bond.

$M^1$, $M^2$, $M^3$ and $M^4$ are particularly preferably identical or different and are —CO—O—, —O—CO—, —$CH_2$—O—, —O—$CH_2$— or a single bond.

$A^1$, $A^2$, $A^3$ and $A^4$ are preferably identical or different and are 1,4-phenylene, in which one or two H atoms may be replaced by F and/or CN, pyridine-2,5-diyl, in which one or two H atoms may be replaced by F and/or CN, pyrimidine-2,5-diyl, in which one or two H atoms may be replaced by F, trans-1,4-cyclohexylene, in which one or two H atoms may be replaced by CN and/or $CH_3$ and/or F, 1,3,4-thiadiazole-2,5-diyl, 1,3-dioxane-2,5-diyl, 1,3-thiazole-2,4-diyl, in which one H atom may be replaced by F and/or CN, 1,3-thiazole-2,5-diyl, in which one H atom may be replaced by F and/or CN, and thiophene-2,5-diyl, in which one or two H atoms may be replaced by F and/or CN.

$A^1$, $A^2$, $A^3$ and $A^4$ are particularly preferably identical or different and are 1,4-phenylene, in which one or two H atoms may be replaced by F, pyridine-2,5-diyl, in which one H atom may be replaced by F, pyrimidine-2,5-diyl, and trans-1,4-cyclohexylene, in which one or two H atoms may be replaced by CN and/or $CH_3$ and/or F.

Very particularly preferred for 6,7-difluoro-1,2,3,4-tetrahydronaphthalene derivatives are the following compounds of the formulae (Ia) to (It):

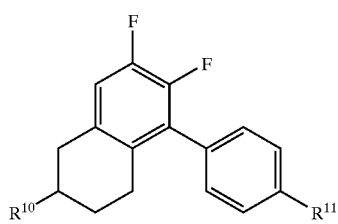
(Ia)

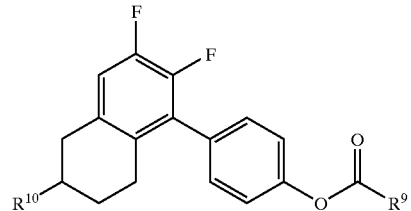
(Ib)

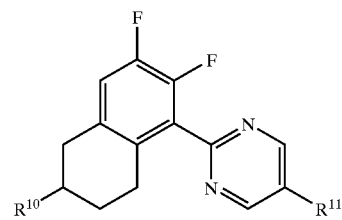
(Ic)

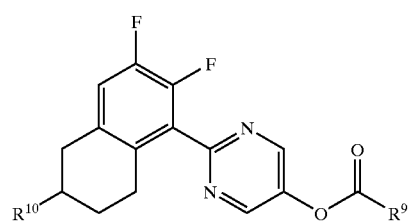
(Id)

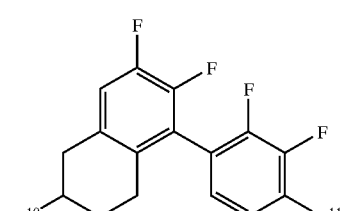
(Ie)

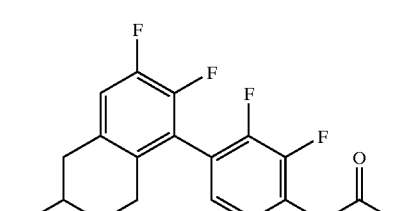
(If)

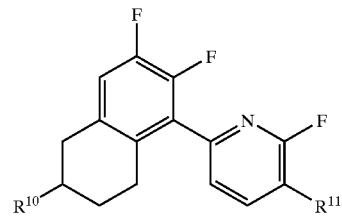
(Ig)

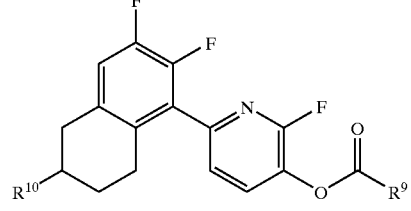
(Ih)

-continued

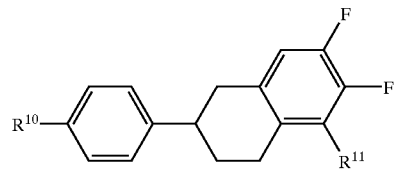
(Ii)

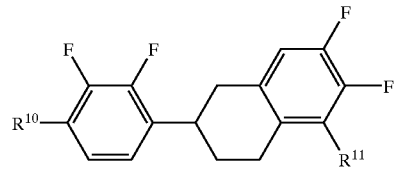
(Ij)

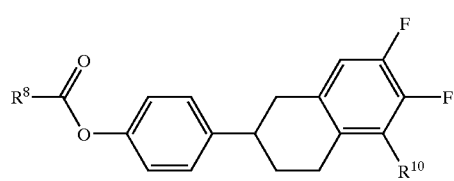
(Ik)

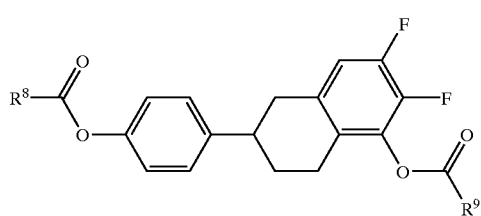
(IL)

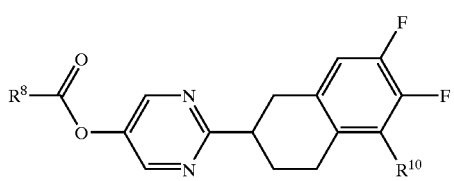
(Im)

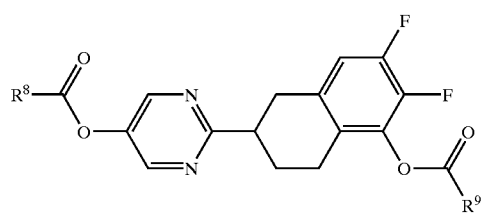
(In)

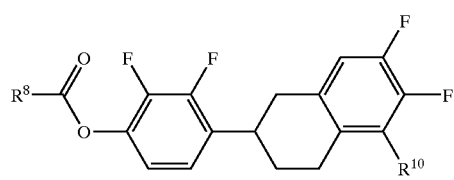
(Io)

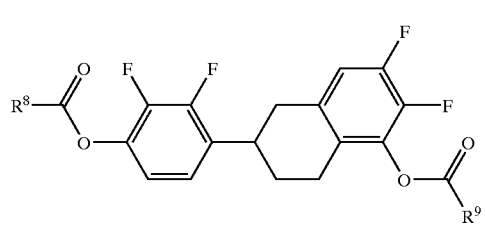
(Ip)

-continued

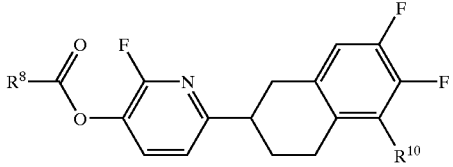
(Iq)

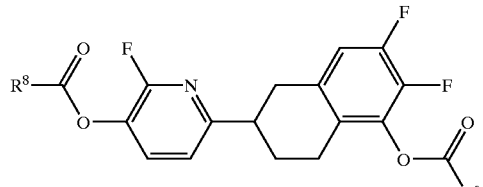
(Ir)

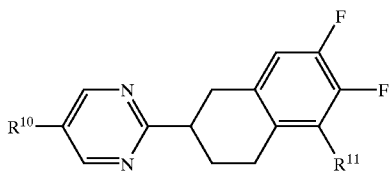
(Is)

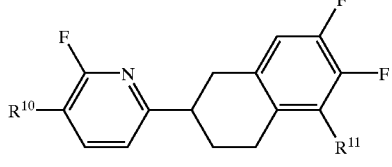
(It)

in which $R^8$ and $R^9$ are identical or different and are a straight-chain or branched alkyl chain having 1 to 19 carbon atoms, in which one or two hydrogen atoms may be replaced by F, and $R^{10}$ and $R^{11}$ are identical or different and are a straight-chain or branched alkyl or alkoxy chain having 1 to 20 or 1 to 19 carbon atoms respectively, in which one or two hydrogen atoms may be replaced by F.

Very particularly preferred for 1,1,6,7-tetrafluoro-1,2,3,4-tetrahydronaphthalene derivatives are the following compounds of the formulae (Ia) to (It):

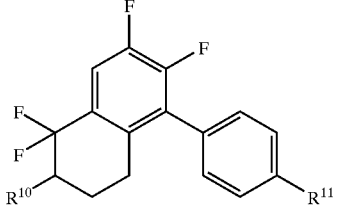
(Ia)

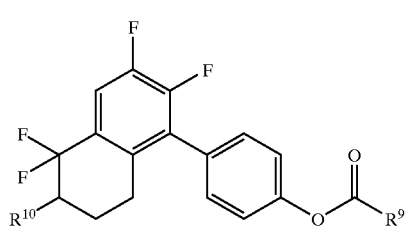
(Ib)

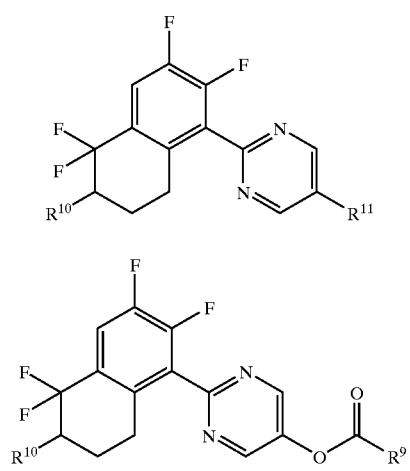
(Ic)
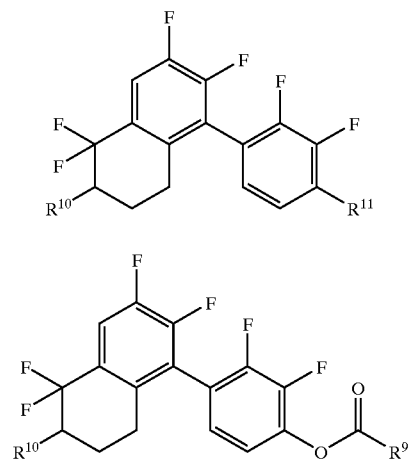
(Id)
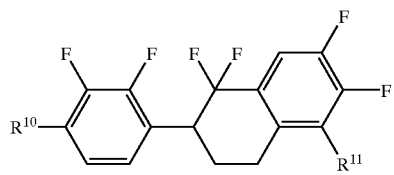
(Ij)
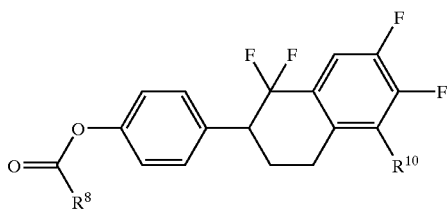
(Ik)
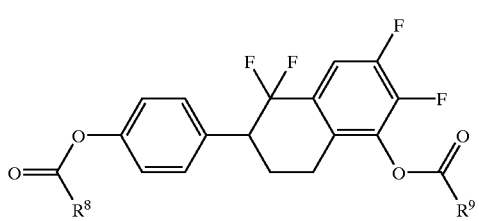
(IL)
(Ie)
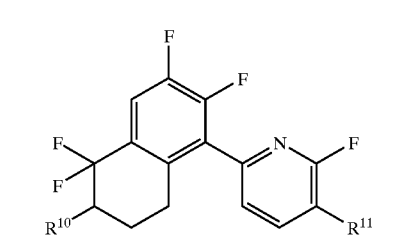
(If)
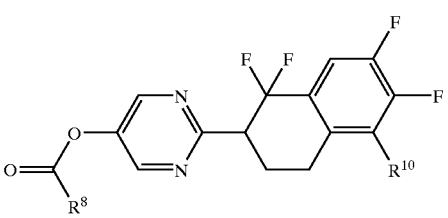
(Im)
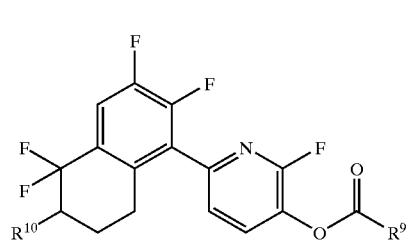
(Ig)
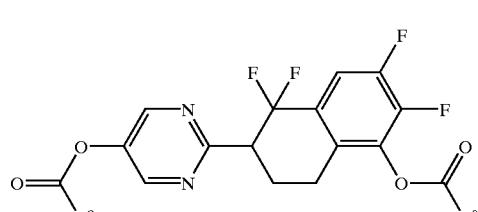
(In)
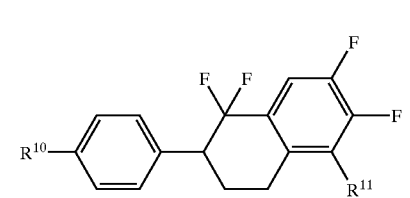
(Ih)
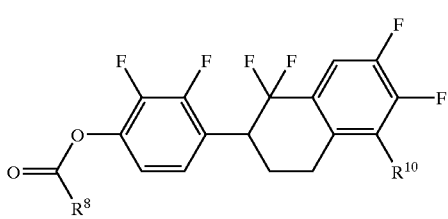
(In)
(Ii)
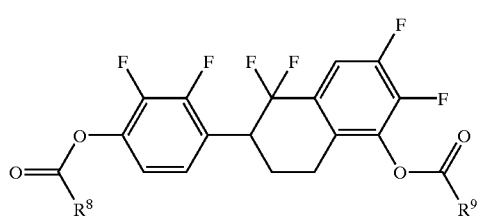
(Ip)

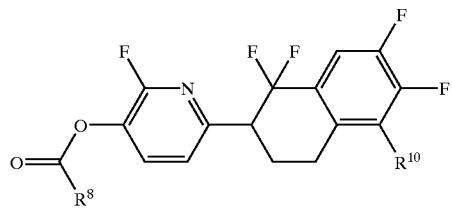
(Iq)

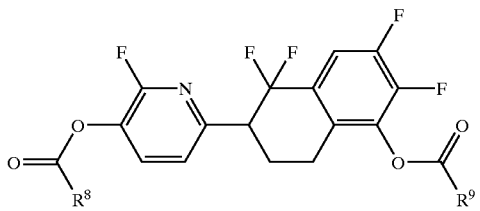
(Ir)

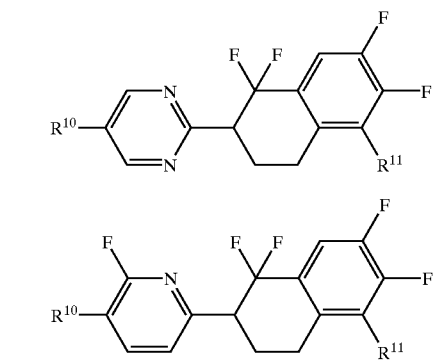
(Is)

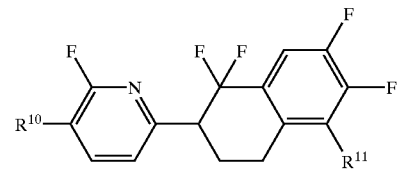
(It)

in which $R^8$ and $R^9$ are identical or different and are a straight-chain or branched alkyl chain having 1 to 19 carbon atoms, in which one or two hydrogen atoms may be replaced by F, and $R^{10}$ and $R^{11}$ are identical or different and are a straight-chain or branched alkyl or alkoxy chain having 1 to 20 or 1 to 19 carbon atoms respectively, in which one or two hydrogen atoms may be replaced by F.

Very particularly preferred for 1,6,7-trifluoronaphthalene derivatives are the following compounds of the formulae (Ia) to (It):

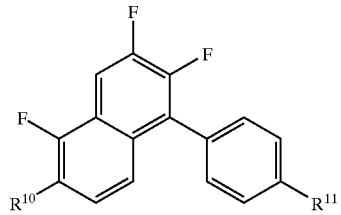
(Ia)

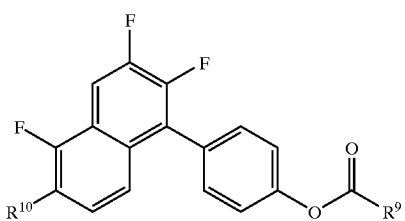
(Ib)

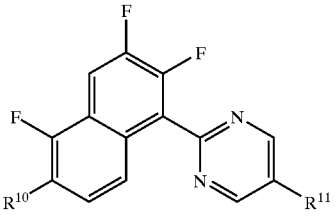
(Ic)

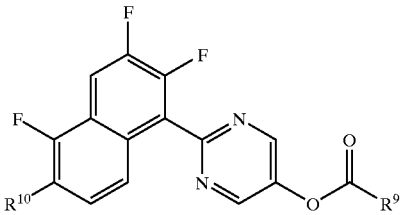
(Id)

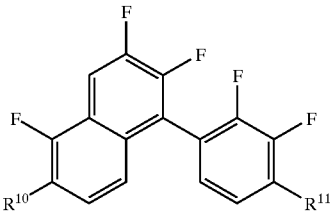
(Ie)

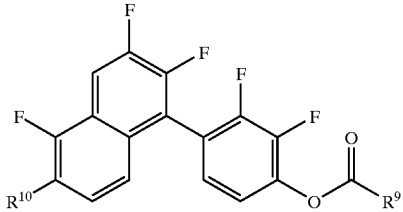
(If)

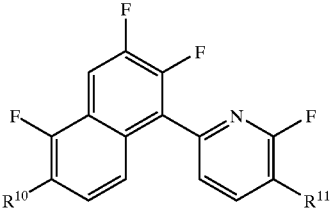
(Ig)

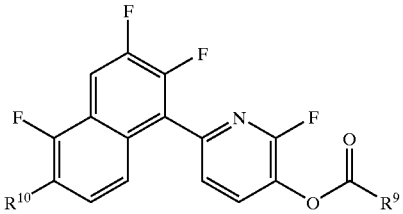
(Ih)

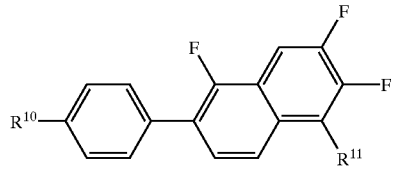
(Ii)

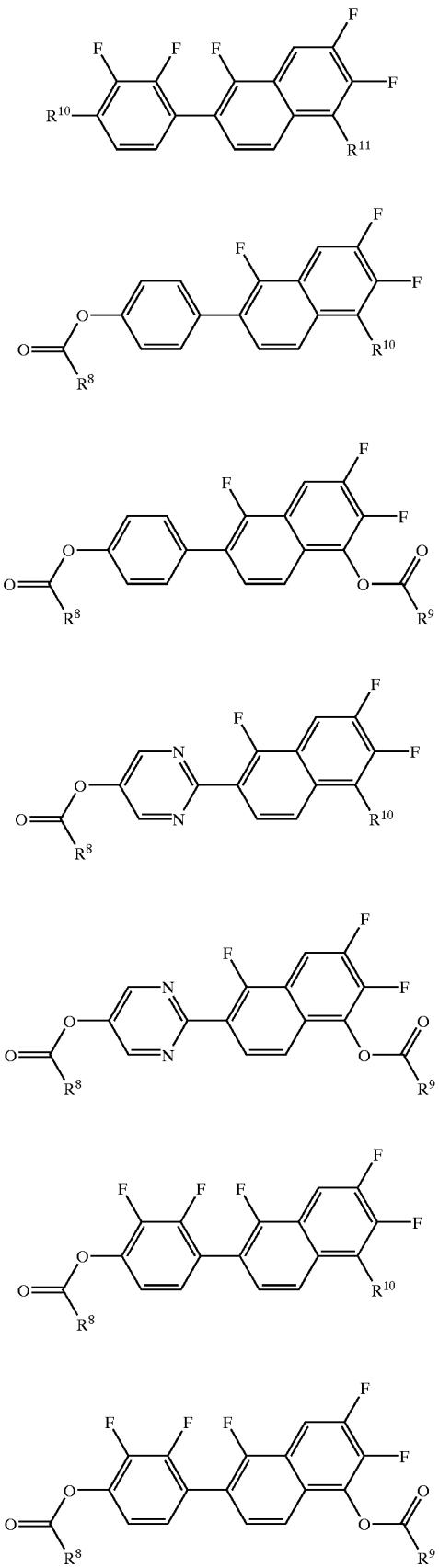

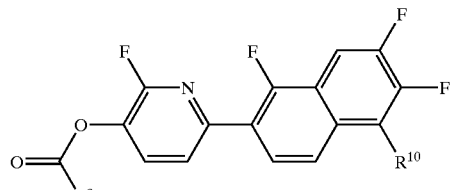

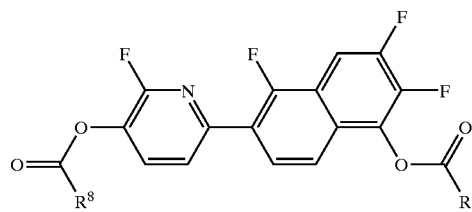

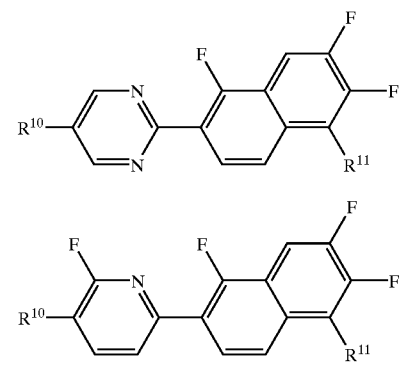

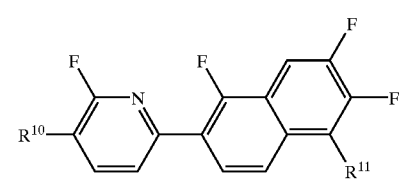

in which $R^8$ and $R^9$ are identical or different and are a straight-chain or branched alkyl chain having 1 to 19 carbon atoms, in which one or two hydrogen atoms may be replaced by F, and $R^{10}$ and $R^{11}$ are identical or different and are a straight-chain or branched alkyl or alkoxy chain having 1 to 20 or 1 to 19 carbon atoms respectively, in which one or two hydrogen atoms may be replaced by F.

Very particularly preferred for 2,3-difluoronaphthalene derivatives are the following compounds of the formulae (Ia) to (It):

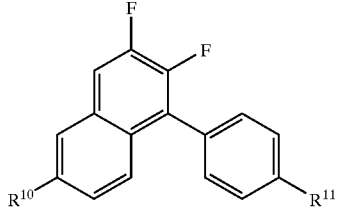

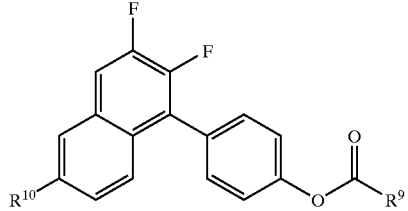

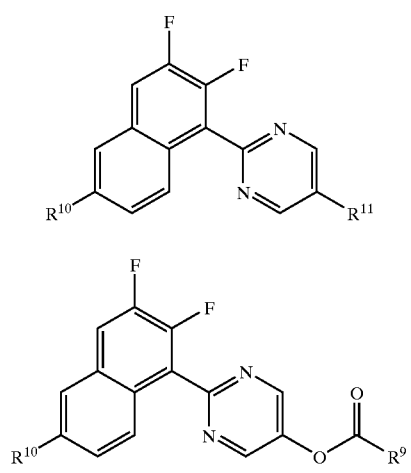
(Ic)
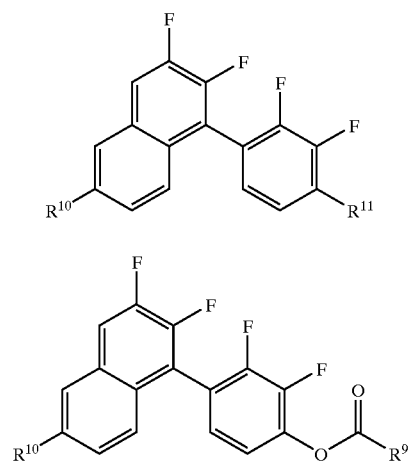
(Id)
(Ie)
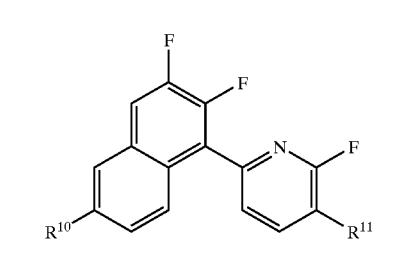
(If)
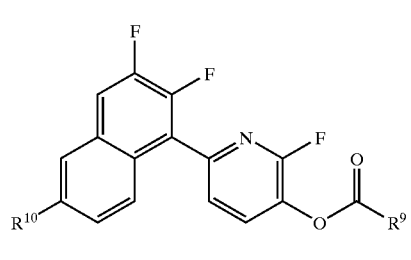
(Ig)
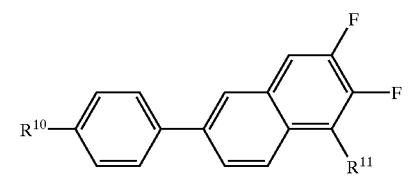
(Ih)
(Ii)
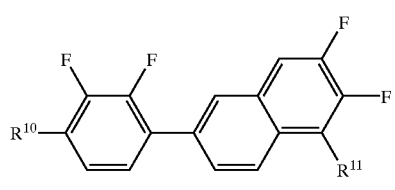
(Ij)
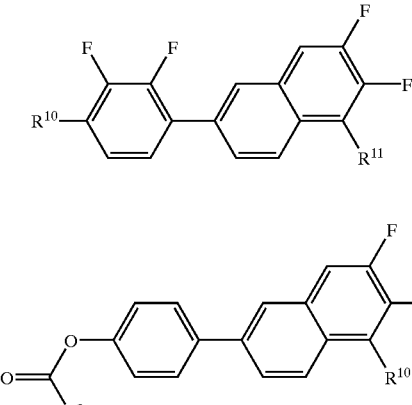
(Ik)
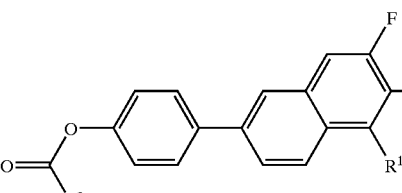
(IL)
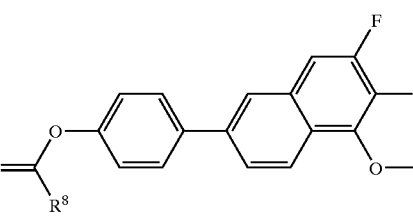
(Im)
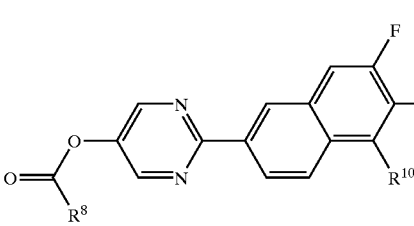
(In)
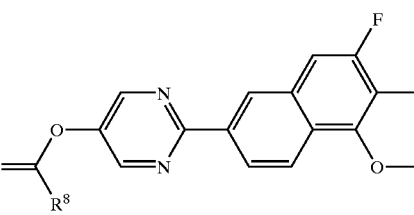
(Io)
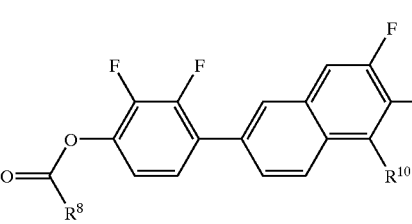
(Ip)
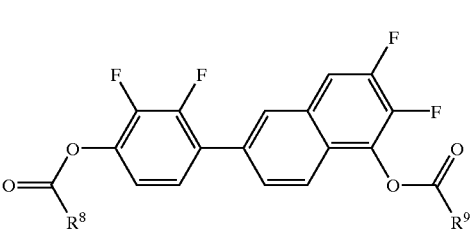

-continued

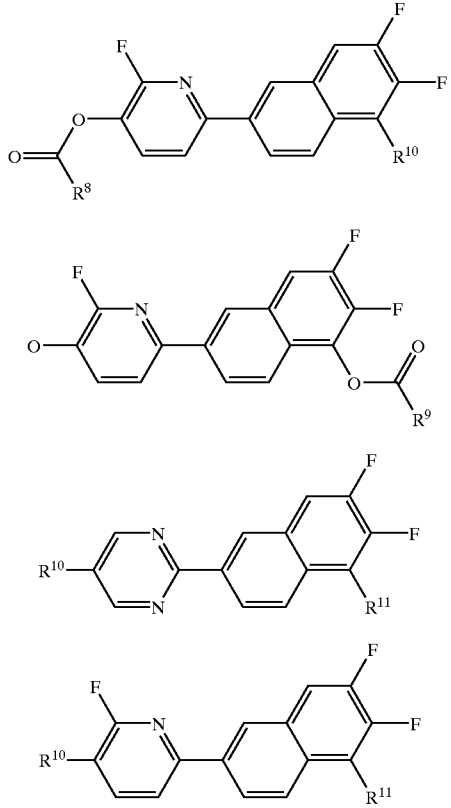

in which $R^8$ and $R^9$ are identical or different and are a straight-chain or branched alkyl chain having 1 to 19 carbon atoms, in which one or two hydrogen atoms may be replaced by F, and $R^{10}$ and $R^{11}$ are identical or different and are a straight-chain or branched alkyl or alkoxy chain having 1 to 20 or 1 to 19 carbon atoms respectively, in which one or two hydrogen atoms may be replaced by F.

The compounds according to the invention are prepared by methods known per se from the literature, as described in the standard works on organic synthesis, for example Houben-Weyl, Methoden der Organischen Chemie [Methods of Organic Chemistry], Georg-Thieme-Verlag, Stuttgart.

The preparation is carried out under reaction conditions which are known and suitable for said reactions. Use can also be made here of variants which are known per se, but are not mentioned here in great detail.

If desired, the starting materials can also be formed in situ by not isolating them from the reaction mixture, but instead immediately converting them further into compounds of the formula (I).

The following schemes show by way of example synthetic routes for the synthesis of 6,7-difluoro-3,4-dihydro-2H-naphthalen-1-one derivatives and further to compounds of the formula (I), although other processes are feasible and possible.

Scheme 1

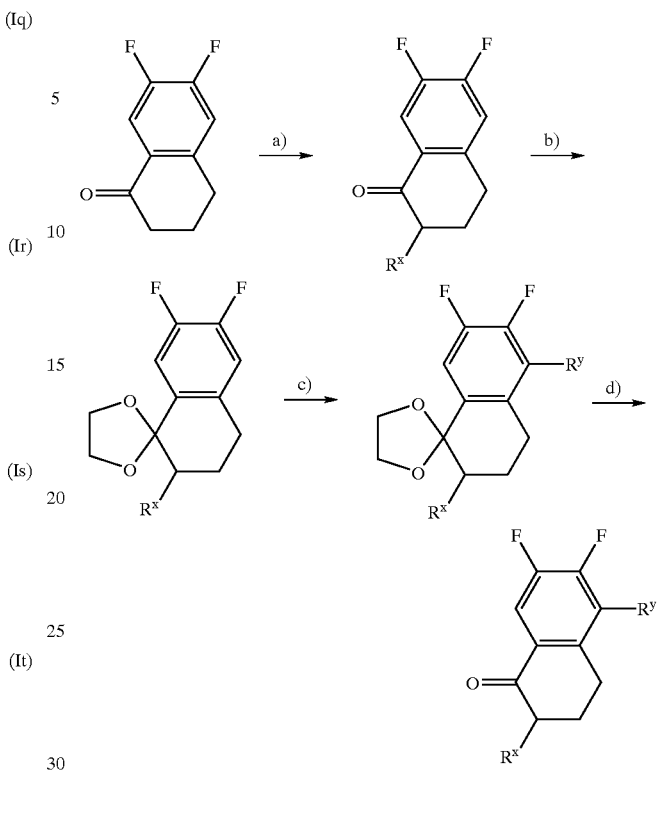

a) analogously to: Rec. Chem. Prog. 1968, 28, 99
b) analogously to: Chem. Ber. 1992, 1865
c) analogously to: Liquid Crystals 1996, 21, 279
d) analogously to: Chem. Ber. 1992, 1865

Scheme 2

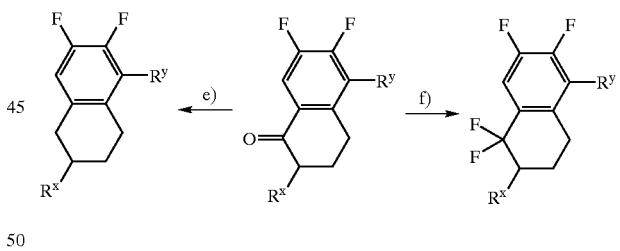

e) analogously to: Org. Prep. Proc. Int. 1980, 12, 13
f) analogously to: J. Org. Chem. 1975, 40, 574

Scheme 3

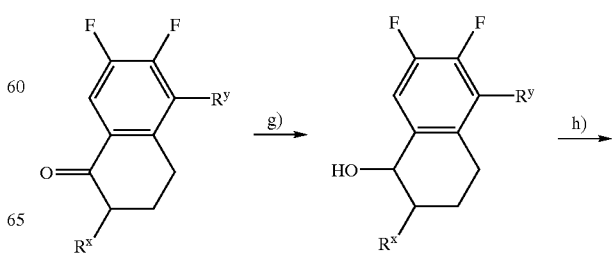

-continued

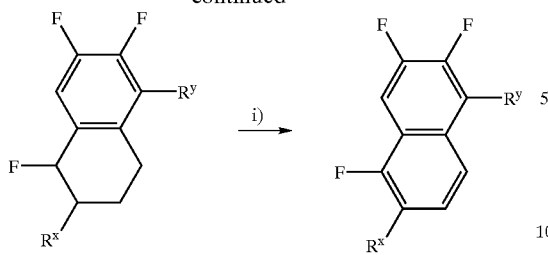

g) analogously to: J. Chem. Soc. 1976, 98, 8114
h) analogously to: J. Org. Chem. 1975, 40, 574
i) analogously to: J. Chem. Soc. 1954, 3569

Scheme 4

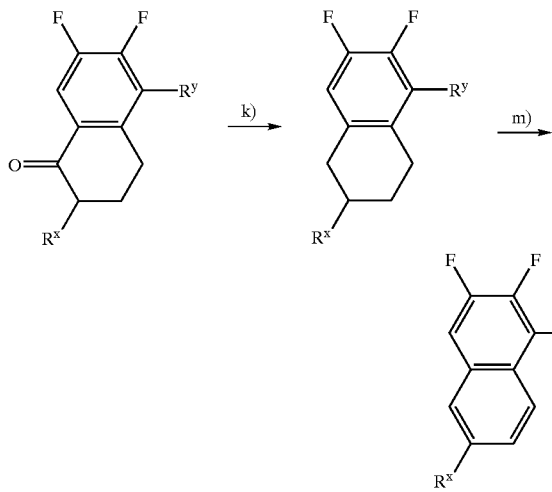

k) analogously to: Org. Prep. Proc. Int. 1980, 12, 13
m) analogously to: J. Chem. Soc. 1954, 3569

Scheme 5

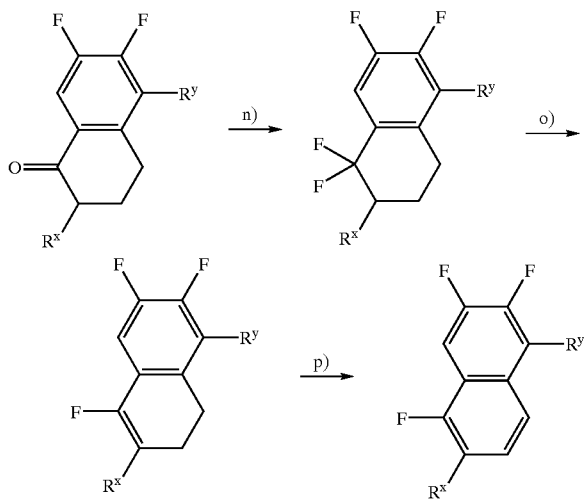

n) analogously to: J. Chem. Soc. 1976, 98, 8114
o) analogously to: DE-A 44 15 881
p) analogously to: J. Chem. Soc. 1954, 3569

Scheme 6

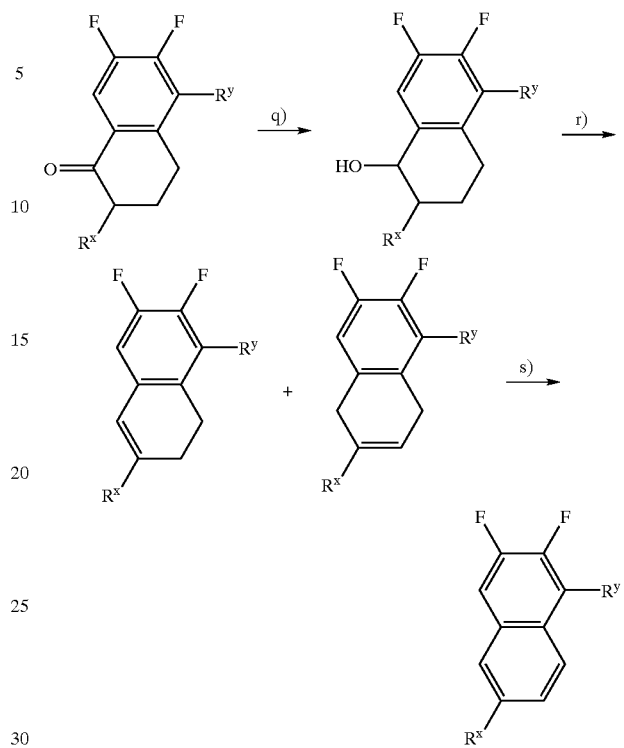

q) analogously to: Liq. Cryst. 1997, 23, 69
r) analogously to: Liq. Cryst. 1997, 23, 69
s) analogously to: J. Chem. Soc. 1954, 3569

The $R^x$ is identical to the group $R^1(-A^1-M^1)_a(-A^2-M^2)_b-$ or a suitable, optionally protected precursor thereof which can be converted into this group in later steps by methods known per se which are familiar to the person skilled in the art. The $R^y$ is identical to the group $(-M^3-A^3)_c(-M^4-A^4)_d-R^2$ or a suitable, optionally protected precursor thereof which can be converted into this group in later steps by methods known per se which are familiar to the person skilled in the art. The preparation is carried out under reaction conditions which are known and suitable for said reactions. Use may also be made here of variants which are known per se, but are not mentioned here in greater detail.

For example, reference may be made to DE-A 23 44 732, 24 50 088, 24 29 093, 25 02 94, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 03 91 203 for compounds containing pyrdine-2,5-diyl groups; DE-A 32 31 462 for compounds containing pyridazine-3,6-diyl groups; EP-A 309 514 for compounds containing 1,3,4-thiadiazole-2,5-diyl groups; WO-A 92/16500 for naphthalene-2,6-diyl groups; K. Seto et al., Journal of the Chemical Society, Chemical Communications 1988, 56, for dioxoborinane-2,5-diyl groups.

The preparation of disubstituted pyridines, disubstituted pyrazines, disubstituted pyrimidines and disubstituted pyridazines is also given, for example, in the corresponding volumes in the series "The Chemistry of Heterocyclic Compounds" by A. Weissberger and E. C. Taylor (Editors).

Dioxane derivatives are advantageously prepared by reaction of a corresponding aldehyde (or a reactive derivative thereof) with a corresponding 1,3-diol (or a reactive derivative thereof), preferably in the presence of an inert solvent, such as benzene or toluene, and/or in the presence of a catalyst, for example a strong acid, such as sulfuric acid, benzenesulfonic acid or p-toluenesulfonic acid, at temperatures from about 20° C. to about 150° C., preferably from 80° C. to 120° C. Primarily suitable reactive derivatives of the starting materials are acetals.

Some of said aldehydes and 1,3-diols and reactive derivatives thereof are known and some can be prepared without difficulty by standard methods of organic chemistry from compounds known from the literature. For example, the aldehydes are obtainable by oxidation of corresponding alcohols or by reduction of nitrites or corresponding carboxylic acids or derivatives thereof, and the diols are obtainable by reduction of corresponding diesters.

Compounds in which an aromatic ring is substituted by at least one F atom can also be obtained from the corresponding diazonium salts by replacement of the diazonium group with a fluorine atom, for example by the methods of Balz and Schiemann.

As far as the linking of ring systems to one another is concerned, reference may be made, for example to the following:

N. Miyaura, T. Yanagai and A. Suzuki in Synthetic Communications 11 (1981), 513–519, DE-C 39 30 663, M. J. Sharp, W. Cheng, V. Snieckus in Tetrahedron Letters 28 (1987) 5093; G. W. Gray in J. Chem. Soc. Perkin Trans II 1989, 2041 and Mol. Cryst. Liq. Cryst. 172 (1989) 165, 204 (1991) 43 and 91; EP-A 0 449 015; WO-A 89/12039; WO-A 89/03821; EP-A 0 354 434 and EP-A 0 694 530 for the direct linking of aromatics and heteroaromatics; DE-A 32 01 721 for compounds containing —CH$_2$CH$_2$— bridges, and Koji Seto et al. in Liquid Crystals 8 (1990) 861–870, for compounds containing —C≡C— bridging members.

Esters of the formula (I) can also be obtained by esterification of corresponding carboxylic acids (or reactive derivatives thereof) using alcohols or phenols (or reactive derivatives thereof, by the DCC method (DCC= dicyclohexylcarbodiimide) or analogously to DE-A 44 27 198. The corresponding carboxylic acids and alcohols or phenols are known and can be prepared analogously to known processes.

Particularly suitable reactive derivatives of said carboxylic acids are the acid halides, especially the chlorides and bromides, furthermore the anhydrides, for example also mixed anhydrides, azides or esters, in particular alkyl esters having 1–4 carbon atoms in the alkyl group.

Particularly suitable reactive derivatives of said alcohols and phenols are the corresponding metal alkoxides or phenoxides, preferably of an alkali metal, such as sodium or potassium.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula (I) are obtainable by etherification of corresponding hydroxyl compounds, preferably corresponding phenols, where the hydroxyl compound is advantageously first converted into a corresponding metal derivative, for example into the corresponding alkali metal alkoxide or alkali metal phenoxide by treatment with NaH, NaNH$_2$, NaOH, KOH, Na$_2$CO$_3$ or K$_2$CO$_3$. This alkali metal compound can then be reacted with the corresponding alkyl halide, alkyl sulfonate or dialkyl sulfate, advantageously in an inert solvent, such as acetone, 1,2-dimethoxyethane, DMF or dimethyl sulfoxide, or alternatively with an excess of aqueous or aqueous-alcoholic NaOH or KOH, at temperatures from about 20° to 100° C.

Regarding the synthesis of specific radicals $R^1$ and $R^2$ reference may additionally be made, for example, to EP-A 0 355 008 for compounds having silicon-containing side chains, EP-A 0 292 954 for optically active compounds containing an oxirane ester unit, EP-A 0 263 437 for optically active compounds containing an oxirane ether unit, EP-A 0 361 272 for optically active compounds containing a dioxolane ester unit, EP-A 0 351 746 for optically active compounds containing a dioxolane ether unit, U.S. Pat. No. 5,051,506 for optically active compounds containing a 2,3-difluoroalkoxy unit, U.S. Pat. No. 4,798,680 for optically active compounds containing a 2-fluoroalkoxy unit, U.S. Pat. No. 4,855,429 for optically active compounds an α-chlorocarboxyl unit, EP-A 0 552 658 for compounds containing cyclohexylpropionyl radicals, and EP-A 0 318 423 for compounds containing cyclopropyl groups in the side chain.

The invention also relates to the use of compounds of the formula (I) in liquid-crystal mixtures, preferably smectic and nematic mixtures, particularly preferably ferroelectric mixtures.

Particular preference is given to the use in ferroelectric liquid-crystal mixtures operated in inverse mode.

The invention furthermore relates to liquid-crystal mixtures, preferably smectic and nematic mixtures, particularly preferably ferroelectric and antiferroelectric mixtures, especially ferroelectric mixtures, comprising one or more compounds of the formula (I).

The smectic or nematic liquid-crystal mixtures according to the invention are preferably suitable for use in electrooptical displays, in the case of nematic mixtures particularly for "active matrix displays" and "in-plane switching displays" (IPS-LCDs), in the case of smectic liquid-crystal mixtures for ECB (electrically controlled birefringence) displays, for electroclinic displays and chiral tilted smectic (ferroelectric and antiferroelectric) displays.

The liquid-crystal mixtures according to the invention generally comprise from 2 to 35 components, preferably from 2 to 25 components, particularly preferably from 2 to 20 components.

They generally comprise from 0.01 to 80% by weight, preferably from 0.1 to 60% by weight, particularly preferably from 0.1 to 30% by weight, of one or more, preferably 1 to 10, particularly preferably 1 to 5, very particularly preferably 1 to 3, of the compounds of the formula (I) according to the invention.

Further components of liquid-crystal mixtures comprising compounds of the formula (I) according to the invention are preferably selected from known compounds having smectic and/or nematic and/or cholesteric phases. These include, for example:

derivatives of phenylpyrimidine, as described, for example, in WO-A-86/06401 and U.S. Pat. No. 4,874, 542, meta-substituted aromatic compounds having a six-membered ring, as described, for example, in EP-A 0 578 054, silicon compounds, as described, for example, in EP-A 0 355 008, mesogenic compounds having only one side chain, as described, for example, in EP-A 0 541 081, hydroquinone derivatives, as described, for example, in EP-A 0 603 786, phenylbenzoates, as described, for example, in P. Keller, Ferroelectrics 58 (1984), 3, and J. W. Goodby et al., Liquid Crystals and Ordered Fluids, Vol. 4, New York, 1984, and thiadiazoles, as described, for example, in EP-A 0 309 514.

Examples of suitable chiral, non-racemic dopants are the following:

optically active phenylbenzoates, as described, for example, in P. Keller, Ferroelectrics 58 (1984), 3, and J. W. Goodby et al., Liquid Crystals and Ordered Fluids, Vol. 4, New York, 1984, optically active oxirane ethers, as described, for example, in EP-A 0 263 437 and WO-A 93/13093, optically active oxirane esters, as described, for example, in EP-A 0 292 954, optically active dioxolane ethers, as described, for example, in EP-A 0 351 746, optically active dioxolane esters, as described, for example, in EP-A 0 361 272, optically active tetrahydrofuran-2-carboxylic esters, as described, for example, in EP-A 0 355 561, and optically active 2-fluoroalkyl ethers, as described, for example, in EP-A 0 237 007, EP-A 428 720 and U.S. Pat. No. 5,051,506.

Suitable further mixture components are listed, in particular, in international patent application PCT/EP 96103154, which is expressly incorporated herein by way of reference.

Preferred further components of FLC mixtures employed in inverse mode are the following:

phenanthrene derivatives of the formula (II)

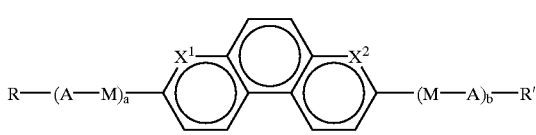

(II)

fluoropyridines of the formula (III)

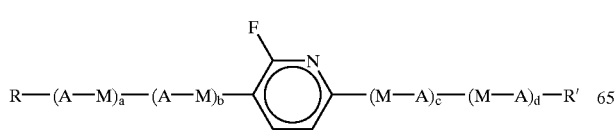

((III)

difluorophenylene derivatives of the formula (IV)

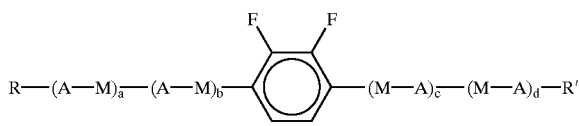

((IV)

meta-substituted aromatic compounds of the formula (V)

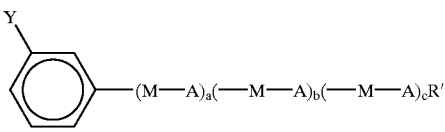

(V)

4-cyanocyclohexyls of the formula (VI)

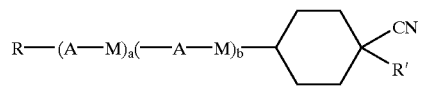

(VI)

1,3,4-thiadiazoles of the formula (VII)

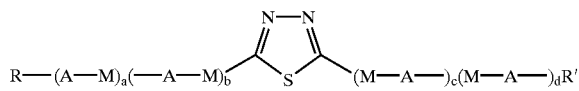

(VII)

where the symbols and indices have the following meanings:

$X^1$ and $X^2$ are identical or different and are, independently of one another, CH, CF or N;

Y is F, $CF_3$ or R;

R and R' are identical or different and are, independently of one another, as defined for $R^1$ and $R^2$ in the formula (I);

A and M are identical or different and are, independently of one another, as defined in the formula (I), and a, b, c and d are identical or different and are, independently of one another, 0 or 1, with the proviso that the compounds can contain not more than four ring systems and, with the exception of the formula (II), must contain at least two ring systems.

The mixtures can in turn be used in electro-optical or fully optical elements, for example display elements, switching elements, light modulators, elements for image processing and/or signal processing or generally in the area of nonlinear optics.

The mixtures are furthermore suitable for field treatment, i.e. for operation in the quasi-bookshelf geometry (QBG) (see, for example, H. Rieger et al., SID 91 Digest (Anaheim), 1991, 396).

The ferroelectric mixtures according to the invention are particularly suitable for operation in so-called inverse or $\tau V_{(min)}$ mode (see, for example, J. C. Jones, M. J. Towler, J. R. Hughes, Displays 1993, 14, No. 2, 86–93; M. Koden, Ferroelectrics 1996, 179, 121–129).

Liquid-crystalline mixtures comprising compounds of the general formula (I) are particularly suitable for use in electro-optical switching and display devices (displays). These displays are usually constructed in such a way that a liquid-crystal layer is enclosed on both sides by layers which are usually, in this sequence starting from the LC layer, at least one alignment layer, electrodes and a limiting plate (for example of glass). In addition, they can contain spacers, adhesive frames, polarizers and, for color displays, thin color-filter layers. Other possible components are antireflection, passivation, compensation and barrier layers and electric non-linear elements, such as thin-film transistors (TFTs) and metal-insulator-metal (MIM) elements. The structure of liquid-crystal displays has already been described in detail in relevant monographs (see, for example, E. Kaneko, "Liquid Crystal TV Displays: Principles and Applications of Liquid Crystal Displays", KTK Scientific Publishers, 1987).

The invention therefore furthermore relates to a switching and/or display device, preferably a smectic or nematic switching and/or display device, in particular a ferroelectric switching and/or display device, containing a liquid-crystal mixture comprising one or more compounds of the formula (I).

In devices which contain a nematic liquid-crystal mixture, active matrix displays and in-plane switching displays (IPS-LCDs) are preferred.

In devices which contain a smectic liquid-crystal mixture, ECB (electrically controlled birefringence) displays, electroclinic displays and chiral tilted smectic (ferroelectric or antiferroelectric) displays are preferred.

Such displays can be used, for example, as computer displays or in smart cards.

A ferroelectric switching and/or display device according to the invention is preferably operated in normal or inverse mode.

Ferroelectric switching and/or display devices operated by multiplex addressing can be operated, inter alia, in two different modes, so-called normal mode or so-called inverse mode ($\tau V_{(min)}$ mode). The difference between the two is in the addressing scheme and in the different requirements made of the dielectric tensor of the FLC material, i.e. of the FLC mixture. An overview is given, for example, by J. C. Jones et al. in Displays 1993, 14, No. 2, 86–93, referred to below as "Jones", and in M. Koden in Ferroelectrics 1996, 179, 121–129, and the literature cited therein.

The switching characteristics of an FLC device can generally be represented by a diagram in which the driving voltage (V) is plotted on the horizontal axis and the width of the addressing pulses ($\tau$, time) is plotted on the vertical axis (se Jones, FIGS. 4, 8, 10 and 11).

A switching curve is determined experimentally and divides the V,τ area into a switching region and a non-switching region. The pulse width usually shortens when the voltage is increased. This behavior characterizes so-called normal mode (see, for example, Jones, FIG. 4).

In suitable materials, however, the Vτ curve has a minimum (at voltage $V_{(min)}$), as shown in Jones in FIGS. 8, 10 and 11. This minimum arises from superposition of dielectric and ferroelectric twist. FLC devices are operated in inverse mode if the sum of the row and column driving voltages in the operating temperature range is greater than the minimum on the Vτ curve, i.e. $V_{(row)}+V_{(column)} > V_{(min)}$.

In the present application, various documents are cited, for example in order to illustrate the technical background. All these documents are expressly incorporated herein by way of reference.

The invention is explained in greater detail by the following examples without a limitation being intended thereby.

In the present application, various documents are cited, for example in order to illustrate the technical background to the invention. All these documents are expressly incorporated herein by way of reference.

The invention is explained in greater detail by the following examples, without this being intended to represent a limitation.

A: Examples of 6,7-Difluoro-1,2,3,4-tetrahydronaphthalene Derivatives

EXAMPLE 1

6,7-Difluoro-2-octyl-5-(4-octyloxyphenyl)-1,2,3,4-tetrahydronaphthalene

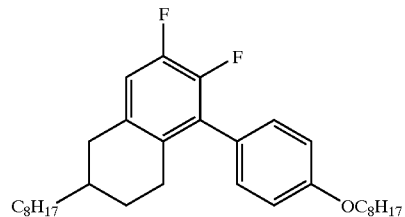

From 6,7-difluoro-5-(4-hydroxyphenyl)-2-octyl-1,2,3,4-tetrahydronaphthalene and 1-octyl bromide by means of the Williamson ether synthesis.

EXAMPLE 2

2-[4-(Butyldimethylsilanyl)butyl]-5-(4-decylphenyl)-6,7-difluoro-1,2,3,4-tetrahydronaphthalene

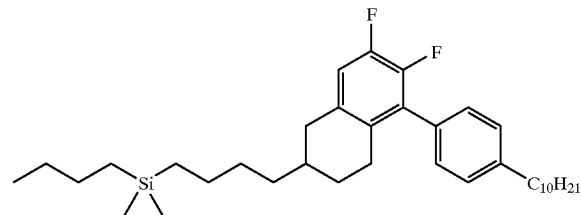

From 6-[4-(butyldimethylsilanyl)butyl]-2,3-difluoro-5,6,7,8-tetrahydronaphthalene-1-boronic acid and 4-bromodecylbenzene by means of the Suzuki coupling.

EXAMPLE 3

6,7-Difluoro-5-(2-fluorodecyloxy)-2-(6-hexyloxypyridin-3-yl)- 1,2,3,4-tetrahydronaphthalene

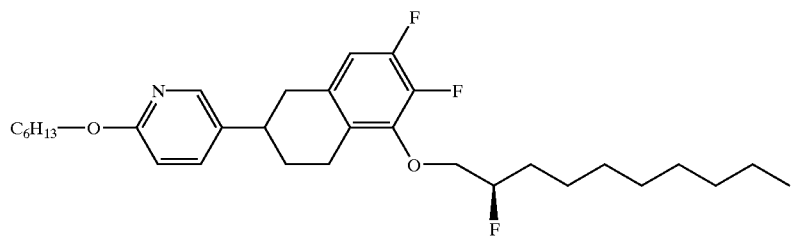

From 6,7-difluoro-2-(6-hexyloxypyridin-3-yl)-5-hydroxy-1,2,3,4-tetrahydronaphthalene and 2-(S)-fluorodecan-1-ol by means of the Mitsunobu reaction.

EXAMPLE 4

6,7-Difluoro-2-(5-hexyloxypyrimidin-2-yl)-5-(3-propyloxiranylmethoxy)-1,2,3,4-tetrahydronaphthalene

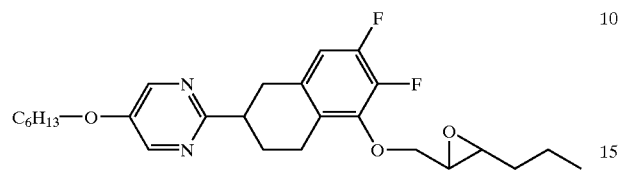

From 6,7-difluoro-2-(5-hexyloxypyrimidin-2-yl)-5-hydroxy-1,2,3,4-tetrahydronaphthalene and (3-propyloxiranyl)methanol by means of the Mitsunobu reaction.

EXAMPLE 5

2,3-Difluoro-6-octyl-5,6,7,8-tetrahydronaphthalen-1-yl 4-Pentylcyclohexanecarboxylate

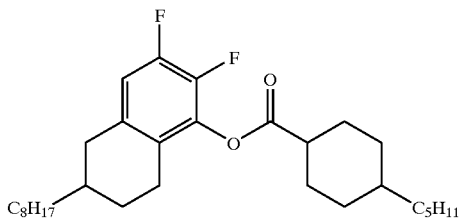

From 6,7-difluoro-5-hydroxy-2-octyl-1,2,3,4-tetrahydronaphthalene and 4-pentylcyclohexanecarboxylic acid by means of DCC esterification.

EXAMPLE 6

6,7-Difluoro-5-octyloxy-2-(4-octyloxyphenyl)-1,2,3,4-tetrahydronaphthalene

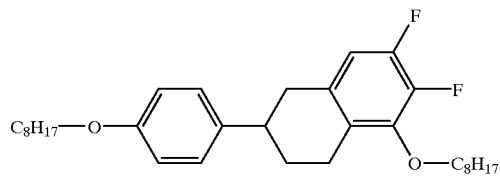

From 6,7-difluoro-5-hydroxy-2-(u-octyloxyphenyl)-1,2,3,4-tetrahydronaphthalene and 1-octyl bromide by means of the Williamson ether synthesis.

B: Examples of 1,1,6,7-tetrafluoro-1,2,3,4-tetrahydronaphthalene derivatives:

EXAMPLE 1

1,1,6,7-Tetrafluoro-2-octyl-5-(4-octyloxyphenyl)-1,2,3,4-tetrahydronaphthalene

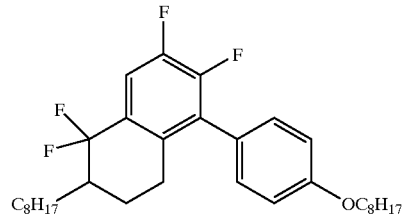

From 4-(2,3,5,5-tetrafluoro-6-octyl-5,6,7,8-tetrahydronaphthalen-1-yl)phenol and 1-octyl bromide by the Williamson ether synthesis.

EXAMPLE 2

Butyl{4-[5-(4-decylphenyl)-1,1,6,7-tetrafluoro-1,2,3,4-tetrahydronaphthalen-2-yl]butyl}dimethylsilane

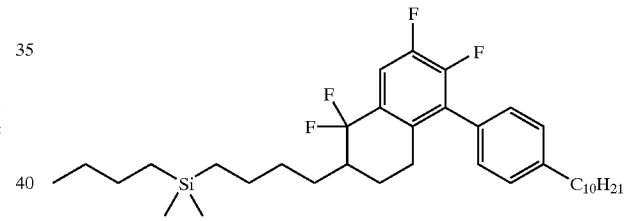

From 6-[4-(butyldimethylsilanyl)butyl]-2,3,5,5-tetrafluoro-5,6,7,8-tetrahydronaphthalene-1-boronic acid and u-bromodecylbenzene by means of the Suzuki coupling.

EXAMPLE 3

2-Hexyloxy-5-[1,1,6,7-tetrafluoro-5-(2-fluorodecyloxy)-1,2,3,4-tetrahydronaphthalen-2-yl]pyridine

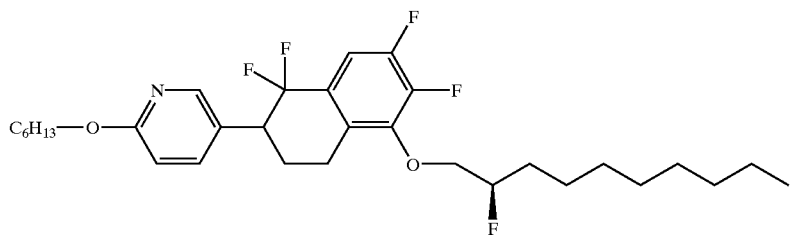

31

From 2,3,5,5-tetrafluoro-6-(6-hexyloxypyridin-3-yl)-5,6,7,8-tetrahydronaphthalen-1-ol and 2-(S)-fluorodecan-1-ol by means of the Mitsunobu reaction.

EXAMPLE 4

5-Hexyloxy-2-[1,1,6,7-tetrafluoro-5-(3-propyloxiranylmethoxy)-1,2,3,4-tetrahydronaphthalen-2-yl]pyrimidine

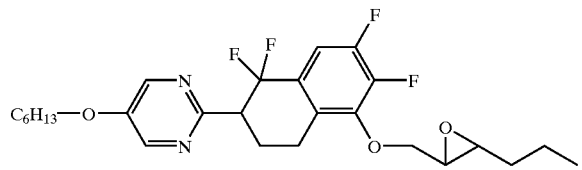

From 2,3,5,5-tetrafluoro-6-(5-hexyloxypyrimidin-2-yl)-5,6,7,8-tetrahydronaphthalen-1-ol and (3-propyloxiranyl)methanol by means of the Mitsunobu reaction.

EXAMPLE 5

2,3,5,5-Tetrafluoro-6-octyl-5,6,7,8-tetrahydronaphthalen-1-yl 4-Pentylcyclohexanecarboxylate

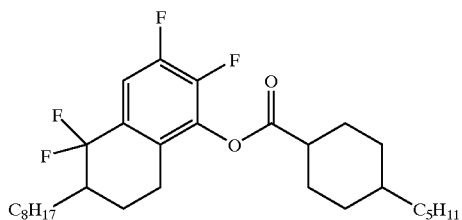

From 2,3,5,5-tetrafluoro-6-octyl-5,6,7,8-tetrahydronaphthalen-1-ol and 4-pentylcyclohexanecarboxylic acid by means of DCC esterification.

32

EXAMPLE 6

1,1,6,7-Tetrafluoro-5-octyloxy-2-(4-octyloxyphenyl)-1,2,3,4-tetrahydronaphthalene

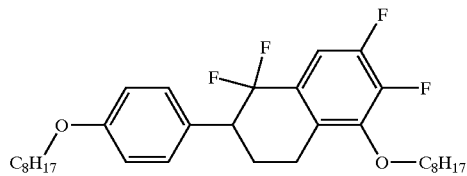

From 2,3,5,5-tetrafluoro-6-(4-octyloxyphenyl)-5,6,7,8-tetrahydronaphthalen-1-ol and 1-octyl bromide by means of the Williamson ether synthesis.

C: Examples of 1,6,7-trifluoronaphthalene derivatives:

EXAMPLE 1

2,3,5-Trifluoro-6-octyl-1-(4-octyloxyphenyl)naphthalene

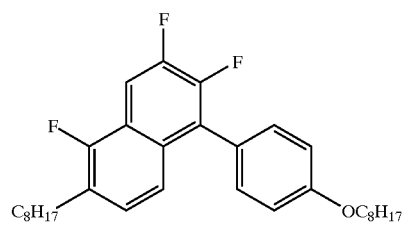

From 4-(2,3,5-trifluoro-6-octylnaphthalen-1-yl)phenol and 1-octyl bromide by means of the Williamson ether synthesis.

EXAMPLE 2

Butyl{4-[5-(4-decylphenyl)-1,6,7-trifluoronaphthalen-2-yl]butyl}dimethylsilane

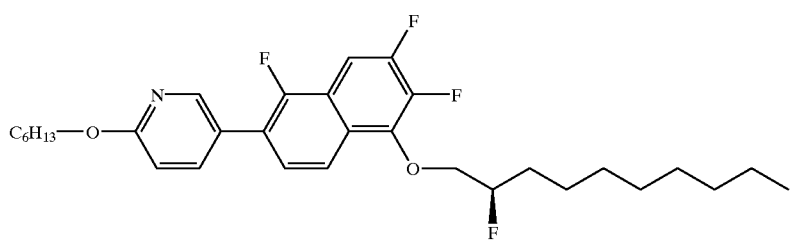

From 6-[4-(butyldimethylsilanyl)butyl]-2,3,5-trifluoronaphthalene-1-boronic acid and 4-bromodecylbenzene by means of the Suzuki coupling.

EXAMPLE 3

2-Hexyloxy-5-[1,6,7-trifluoro-5-(2-fluorodecyloxy)naphthalen-2-yl]pyridine

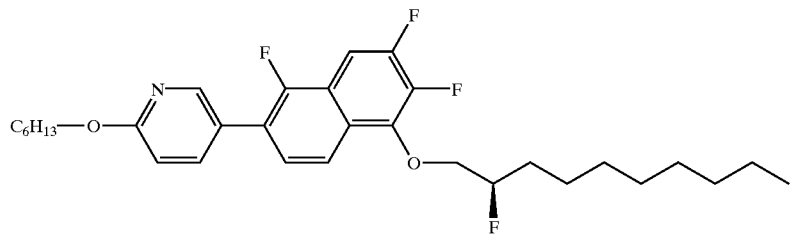

From 2,3,5-trifluoro-6-(6-hexyloxypyridin-3-yl)naphthalen-1-ol and 2-(S)-fluorodecan-1-ol by means of the Mitsunobu reaction.

EXAMPLE 4

5-Hexyloxy-2-[1,6,7-trifluoro-5-(3-propyloxiranylmethoxy)naphthalen-2-yl]-pyrimidine

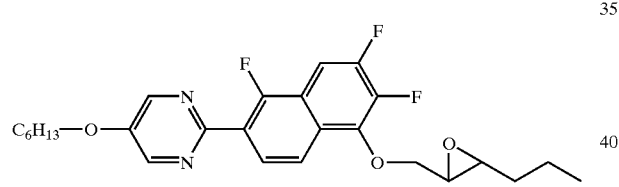

From 2,3,5-trifluoro-6-(5-hexyloxypyrimidin-2-yl)naphthalen-1-ol and (3-propyloxiranyl)methanol by means of the Mitsunobu reaction.

EXAMPLE 5

2,3,5-Trifluoro-6-octylnaphthalen-1-yl 4-Pentylcyclohexanecarboxylate

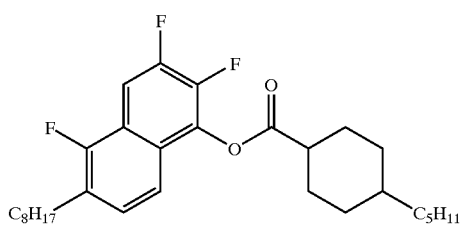

From 2,3,5-trifluoro-6-octylnaphthalen-1-ol and 4-pentylcyclohexanecarboxylic acid by means of DCC esterification.

EXAMPLE 6

2,3,5-Trifluoro-1-octyloxy-6-(4-octyloxyphenyl)naphthalene

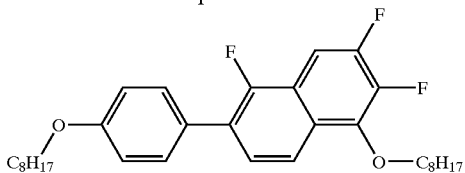

From 2,3,5-trifluoro-6-(4-octyloxyphenyl)naphthalen-1-ol and 1-octyl bromide by means of the Williamson ether synthesis.

D: Examples of 2,3-difluoronaphthalene derivatives:

EXAMPLE 1

2,3-Difluoro-6-octyl-1-(4-octyloxyphenyl)naphthalene

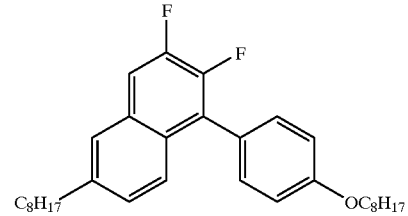

From 4-(2,3-difluoro-6-octylnaphthalen-1-yl)phenol and 1-octyl bromide by means of the Williamson ether synthesis.

EXAMPLE 2

Butyl{4-[5-(4-decylphenyl)-2,3-difluoronaphthalen-2-yl]butyl}dimethylsilane

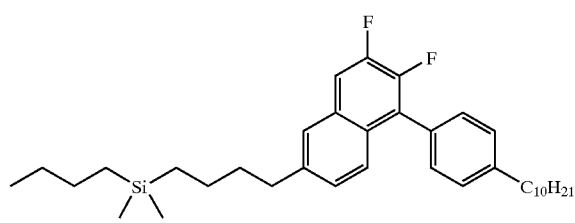

From 6-[4-(butyldimethylsilanyl)butyl]-2,3-difluoronaphthalene-1-boronic acid and 4-bromodecylbenzene by means of the Suzuki coupling.

EXAMPLE 3

2-Hexyloxy-5-[2,3-difluoro-5-(2-fluorodecyloxy)naphthalen-2-yl]pyridine

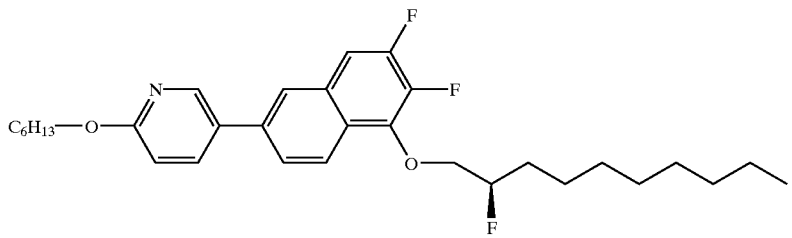

From 2,3-difluoro-6-(6-hexyloxypyridin-3-yl)naphthalen-1-ol and 2-(S)-fluorodecan-1-ol by means of the Mitsunobu reaction.

EXAMPLE 4

2-[6,7-Difluoro-5-(3-propyloxiranylmethoxy)naphthalen-2-yl]-5-hexyloxypyrimidine

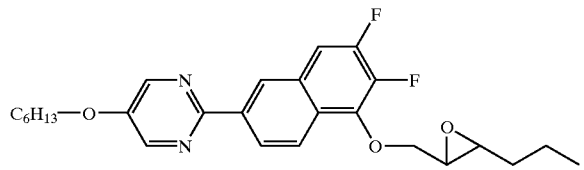

From 2,3-difluoro-6-(5-hexyloxypyrimidin-2-yl)naphthalen-1-ol and (3-propyloxiranyl)methanol by means of the Mitsunobu reaction.

EXAMPLE 5

2,3-Difluoro-6-octylnaphthalen-1-yl 4-pentylcyclohexanecarboxylate

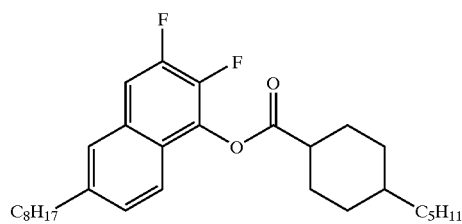

From 2,3-difluoro-6-octylnaphthalen-1-ol and 4-pentylcyclohexanecarboxylic acid by means of DCC esterification.

EXAMPLE 6

2,3-Difluoro-1-octyloxy-6-(4-octyloxyphenyl)naphthalene

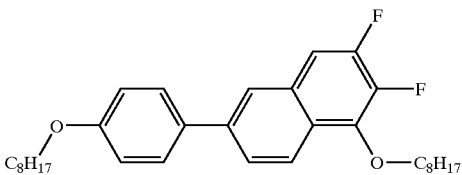

From 2,3-difluoro-6-(4-octyloxyphenyl)naphthalen-1-ol and 1-octyl bromide by means of the Williamson ether synthesis.

What is claimed is:
1. A fluorinated naphthalene derivative of the formula (I)

$$R^1(-A^1-M^1)_a(-A^2-M^2)_b-B-(-M^3-A^3)_c-(M^4-A^4)_d- \atop R^2 \qquad (I)$$

where the symbols and indices are defined as follows:
group B is

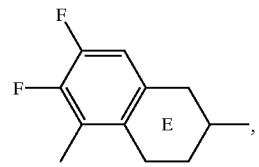

having the meaning

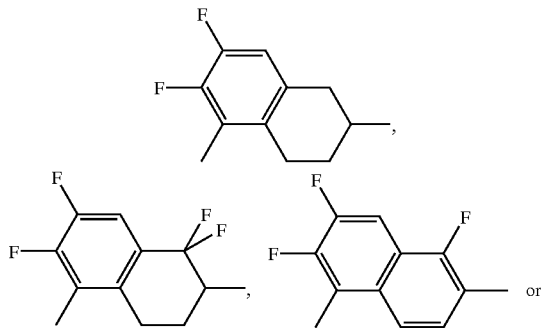

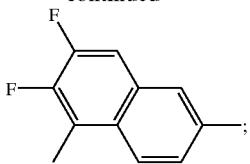

$R^1$ and $R^2$ are identical or different and are
a) hydrogen, $-OCF_3$, $-CF_3$, $-CN$, $-F$, $-Cl$, $-OCHF_2$, $-OCH_2F$, $-CHF_2$ or $-CH_2F$
b) a straight-chain or branched alkyl radical (with or without an asymmetrical carbon atom) having 1 to 20 carbon atoms, where
  b1) one or more non-adjacent and non-terminal $-CH_2-$ groups may be replaced by $-O-$, $-S-$, $-CO-O-$, $-O-CO-$, $-O-CO-O-$ or $-Si(CH_3)_2-$, and/or
  b2) one or more $-CH_2-$ groups may be replaced by $-CH=CH-$, $-C\equiv C-$, cyclopropane-1,2-diyl, 1,4-phenylene, 1,4-cyclohexylene or 1,3-cyclopentylene, and/or
  b3) one or more H atoms may be replaced by F and/or Cl, and/or
  b4) the terminal $-CH_3$ group may be replaced by one of the following chiral groups (optically active or racemic):

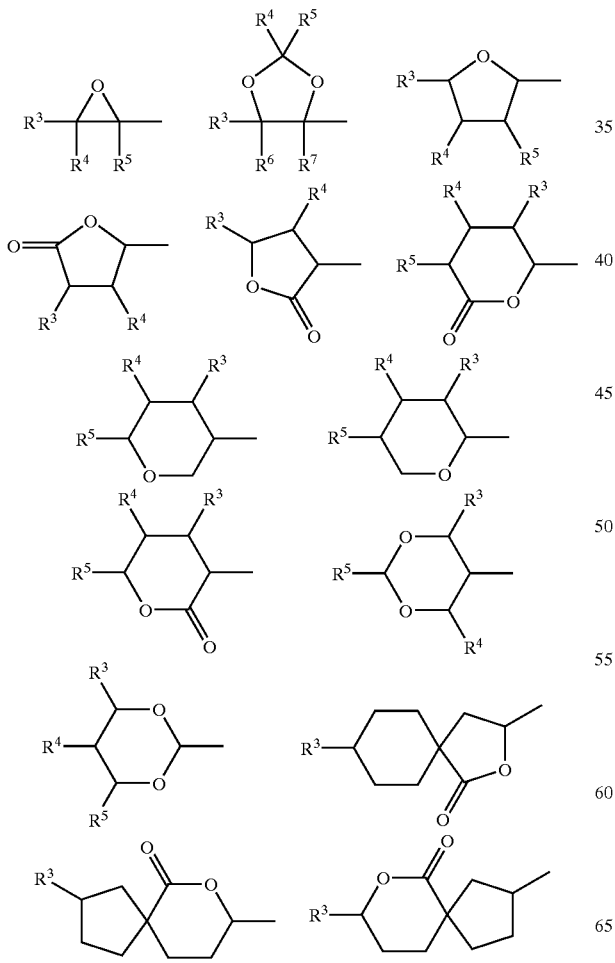

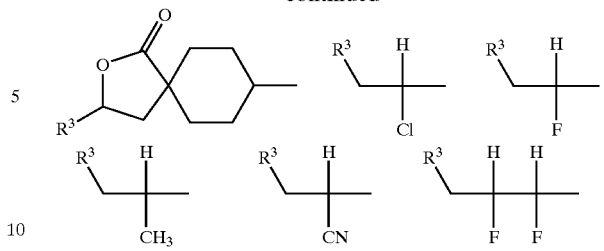

with the proviso that at most one of the radicals $R^1$ and $R^2$ is hydrogen, $-OCF_3$, $-CF_3$, $-CN$, $-F$, $-Cl$, $-OCHF_2$, $-OCH_2F$, $-CHF_2$ or $-CH_2F$;

$R^3$, $R^4$, $R^5$, $R^6$ and $R^7$ are identical or different and are
a) hydrogen
b) a straight-chain or branched alkyl radical (with or without an asymmetrical carbon atom) having 1 to 16 carbon atoms, where
  b1) one or more non-adjacent and non-terminal $-CH_2-$ groups may be replaced by $-O-$, and/or
  b2) one or two $-CH_2-$ groups may be replaced by $-CH=CH-$,
c) $R^4$ and $R^5$ together may alternatively be $-(CH_2)_4-$ or $-(CH_2)_5-$ if they are bonded to an oxirane, dioxolane, tetrahydrofuran, tetrahydropyran, butyrolactone or valerolactone system;

$M^1$, $M^2$, $M^3$ and $M^4$ are identical or different and are $-CO-O-$, $-O-CO-$, $-CO-S-$, $-S-CO-$, $-CS-O-$, $-CS-S-$, $-O-CS-$, $-S-CS-$, $-CH_2-O-$, $-O-CH_2-$, $-CH_2-S-$, $-S-CH_2-$, $-CH=CH-$, $-C\equiv C-$, $-CH_2-CH_2-CO-O-$, $-O-CO-CH_2-CH_2-$ or a single bond;

$A^1$, $A^2$, $A^3$ and $A^4$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, 1,4-cyclohexylene, in which one or two H atoms may be replaced by CN and/or $CH_3$ and/or F, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5-diyl, in which one or two H atoms may be replaced by F, Cl and/or CN, naphthalene-2,6-diyl, in which one or more H atoms may be replaced by F, Cl and/or CN, or 1-alkyl-1-silacyclohexane-1,4-diyl;

a, b, c and d are 0 or 1; with the proviso that the compound of the formula (I) does not contain more than four five- or multi-membered ring systems and when B is a difluoronaphthalene-diyl group the sum of a, b, c, and d is at least 1.

2. A fluorinated naphthalene derivative as claimed in claim 1, where the symbols and indices in the formula (I) have the following meanings:

$R^1$ and $R^2$ are identical or different and are
a) hydrogen,
b) a straight-chain or branched alkyl radical (with or without an asymmetrical carbon atom) having 1 to 18 carbon atoms, where
b1) one or more non-adjacent and non-terminal —CH$_2$— groups may be replaced by —O—, —CO—O—, —O—CO—, —O—CO—O— or —Si(CH$_3$)$_2$—, and/or
b2) one —CH$_2$— group may be replaced by cyclopropane-1,2-diyl, 1,4-phenylene or trans-1,4-cyclohexylene, and/or
b3) one or more H atoms may be replaced by F, and/or
b4) the terminal CH$_3$ group may be replaced by one of the following chiral groups (optically active or racemic):

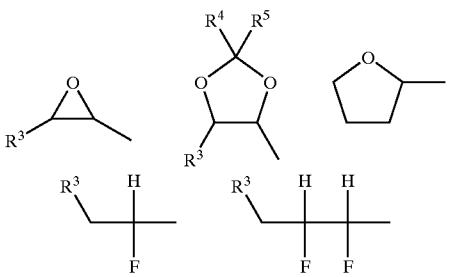

with the proviso that at most one of the radicals $R^1$ and $R^2$ can be hydrogen;

$R^3$, $R^4$, $R^5$, $R^6$ and $R^7$ are identical or different and are
a) hydrogen
b) a straight-chain or branched alkyl radical (with or without an asymmetrical carbon atom) having 1 to 14 carbon atoms, where
b1) one or two non-adjacent and non-terminal —CH$_2$— groups may be replaced by —O—, and/or
b2) one —CH$_2$— group may be replaced by —CH=CH—,
c) $R^4$ and $R^5$ together may alternatively be —(CH$_2$)$_4$— or —(CH$_2$)$_5$— if they are bonded to an oxirane, dioxolane, tetrahydrofuran, tetrahydropyran, butyrolactone or valerolactone system;

$M^1$, $M^2$, $M^3$ and $M^4$ are identical or different and are —C O—O—, —O—C O—, —CH$_2$—O—, —O—CH$_2$—, —CH=CH—, —C≡C—, —CH$_2$—CH$_2$—CO—O—, —O—CO—CH$_2$—CH$_2$— or a single bond;

$A^1$, $A^2$, $A^3$ and $A^4$ are identical or different and are 1,4-phenylene, in which one or two H atoms may be replaced by F and/or CN, pyridine-2,5-diyl, in which one or two H atoms may be replaced by F and/or CN, pyrimidine-2,5-diyl, in which one or two H atoms may be replaced by F, trans-1,4-cyclohexylene, in which one or two H atoms may be replaced by CN and/or CH$_3$ and/or F, 1,3,4-thiadiazole-2,5-diyl, 1,3-dioxane-2,5-diyl, 1,3-thiazole-2,4-diyl, in which one H atom may be replaced by F and/or CN, 1,3-thiazole-2,5-diyl, in which one H atom may be replaced by F and/or CN, and thiophene-2,5-diyl, in which one or two H atoms may be replaced by F and/or CN;

a, b, c and d are 0 or 1; with the proviso that the compound of the formula (I) does not contain more than four five- or multi-membered ring systems.

3. A fluorinated naphthalene derivative as claimed in claim 1, where the symbols and indices in the formula (I) have the following meanings:

$R^1$ and $R^2$ are identical or different and are
a) hydrogen,
b) a straight-chain or branched alkyl radical (with or without an asymmetrical carbon atom) having 1 to 16 carbon atoms, where
b1) one or two non-adjacent and non-terminal —CH$_2$— groups may be replaced by —O—, —CO—O—, —O—CO—, —O—CO—O—or —Si(CH$_3$)$_2$—, and/or
b2) one —CH$_2$— group may be replaced by 1,4-phenylene or trans-1,4-cyclohexylene, and/or
b3) one or more H atoms may be replaced by F, and/or
b4) the terminal CH$_3$ group may be replaced by one of the following chiral groups (optically active or racemic):

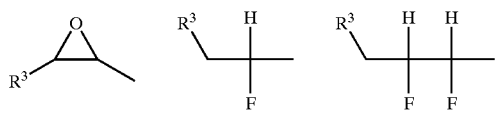

with the proviso that only one of the radicals $R^1$ and $R^2$ can be hydrogen;

$R^3$, $R^4$, $R^5$, $R^6$ and $R^7$ are identical or different and are
a) hydrogen
b) a straight-chain or branched alkyl radical (with or without an asymmetrical carbon atom) having 1 to 14 carbon atoms, where
b1) one non-terminal —CH$_2$— group may be replaced by —O—, and/or
c) $R^4$ and $R^5$ together may alternatively be —(CH$_2$)$_4$— or —(CH$_2$)$_5$— if they are bonded to an oxirane, dioxolane, tetrahydrofuran, tetrahydropyran, butyrolactone or valerolactone system.

$M^1$, $M^2$, $M^3$ and $M^4$ are identical or different and are —CO—O—, —O—CO—, —CH$_2$O—, —O—CH$_2$— or a single bond;

$A^1$, $A^2$, $A^3$ and $A^4$ are identical or different and are 1,4-phenylene, in which one or two H atoms may be replaced by F, pyridine-2,5-diyl, in which one H atom may be replaced by F, pyrimidine-2,5-diyl and trans-1,4-cyclohexylene, in which one or two H atoms may be replaced by CN and/or CH$_3$ and/or F;

a, b, c and d are 0 or 1; with the proviso that the compound of the formula (I) does not contain more than four five- or multi-membered ring systems.

4. A fluorinated naphthalene derivative as claimed in claim 1, for 6,7-difluoro -1,2,3,4-tetrahydronaphthalene derivatives selected from the following group (Ia)–(It):

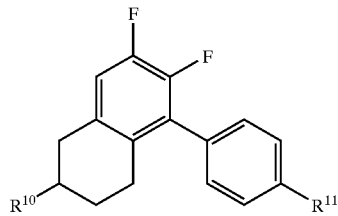

(Ia)

-continued
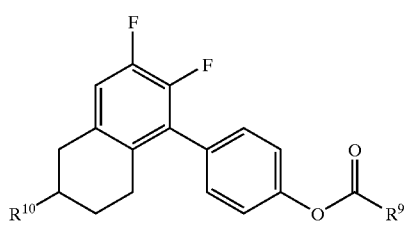
(Ib)
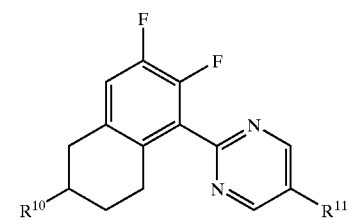
(Ic)
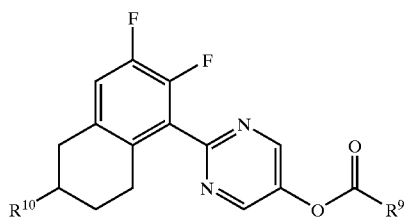
(Id)
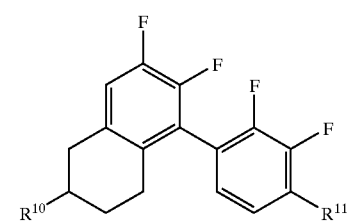
(Ie)
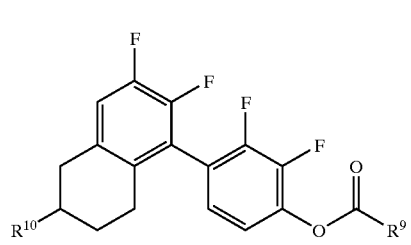
(If)
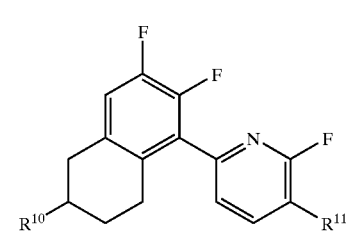
(Ig)
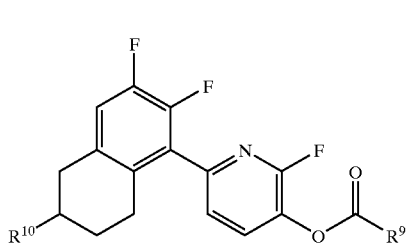
(Ih)
-continued
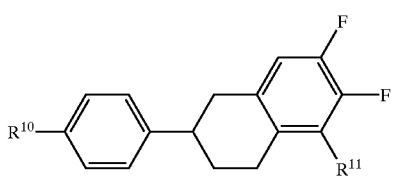
(Ii)
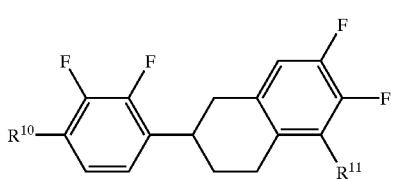
(Ij)
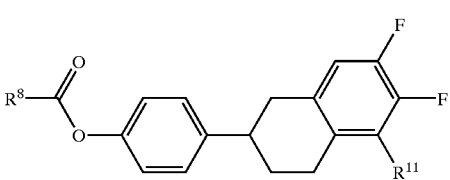
(Ik)
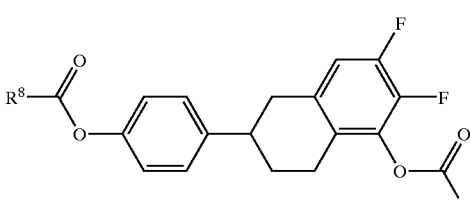
(Il)
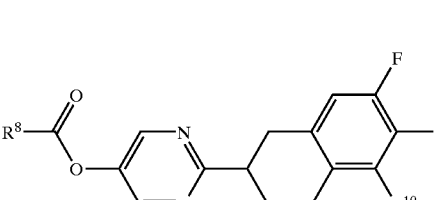
(Im)
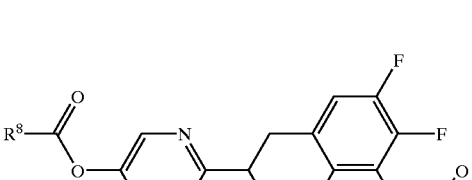
(In)
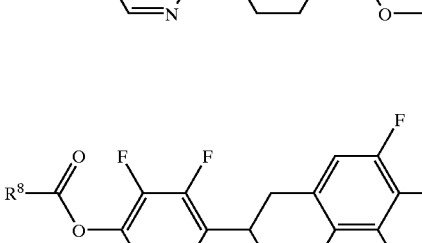
(Io)
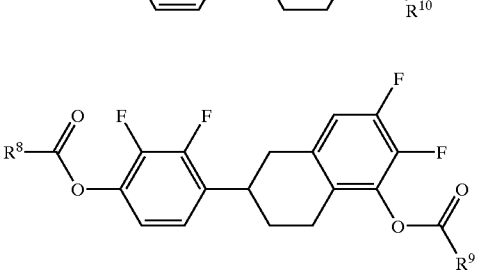
(Ip)

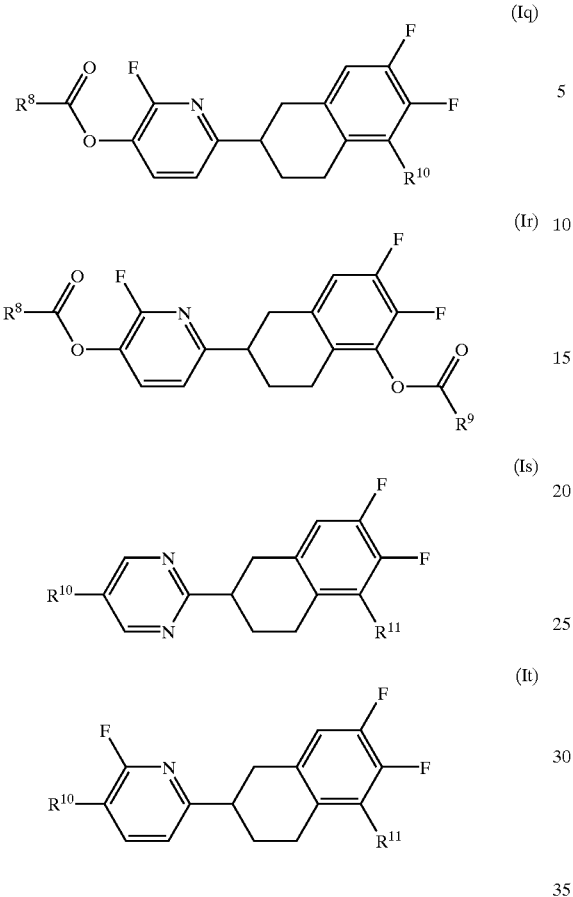

in which $R^8$ and $R^9$ are identical or different and are a straight-chain or branched alkyl chain having 1 to 19 carbon atoms, in which one or two hydrogen atoms may be replaced by F, and $R^{10}$ and $R^{11}$ are identical or different and are a straight-chain or branched alkyl or alkoxy chain having 1 to 20 or 1 to 19 carbon atoms respectively, in which one or two hydrogen atoms may be replaced by F, for 1,1,6,7-tetrafluoro-1,2,3,4-tetrahydronaphthalene derivatives selected from the following group (Ia) to (It):

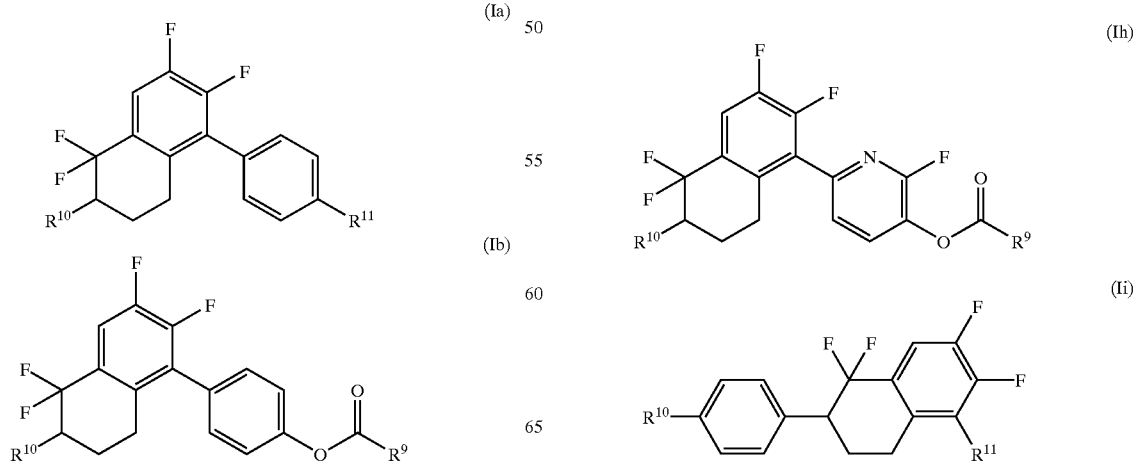

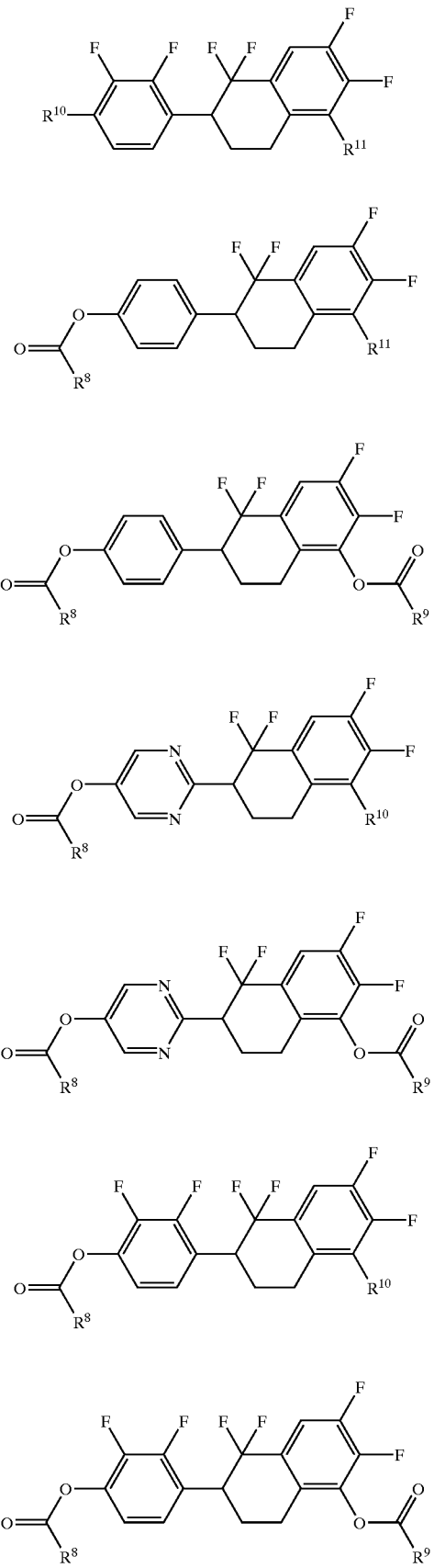

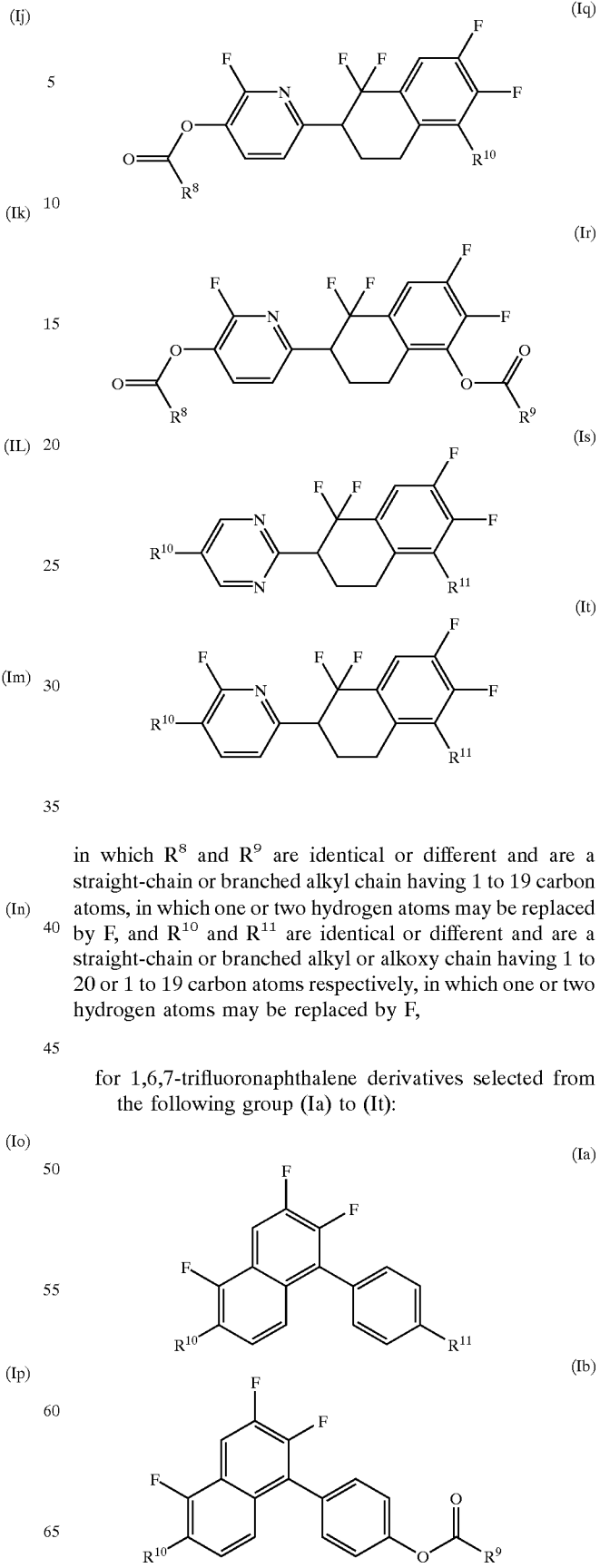

in which $R^8$ and $R^9$ are identical or different and are a straight-chain or branched alkyl chain having 1 to 19 carbon atoms, in which one or two hydrogen atoms may be replaced by F, and $R^{10}$ and $R^{11}$ are identical or different and are a straight-chain or branched alkyl or alkoxy chain having 1 to 20 or 1 to 19 carbon atoms respectively, in which one or two hydrogen atoms may be replaced by F, for 1,6,7-trifluoronaphthalene derivatives selected from the following group (Ia) to (It):

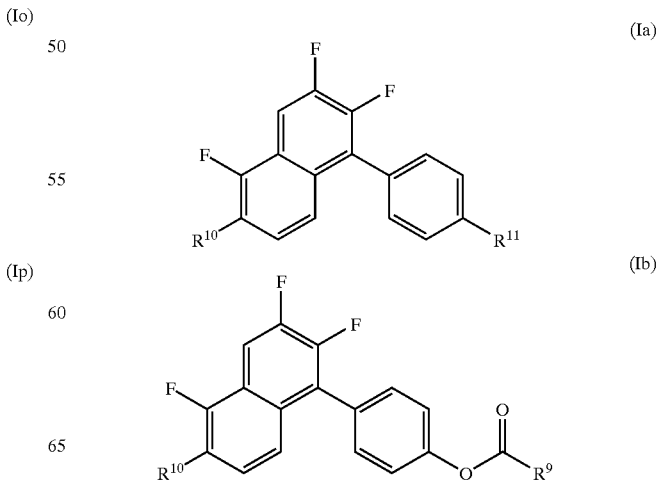

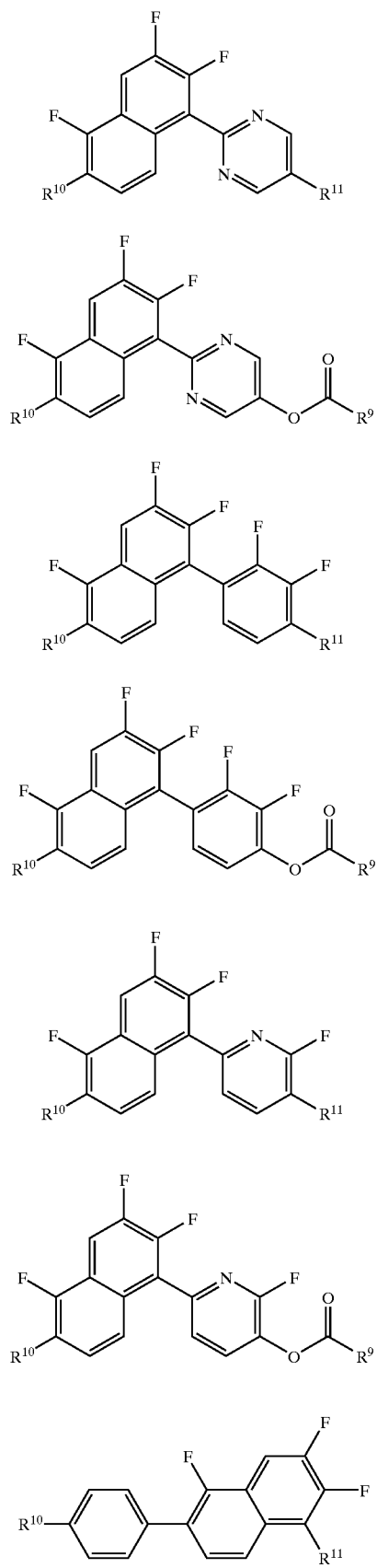
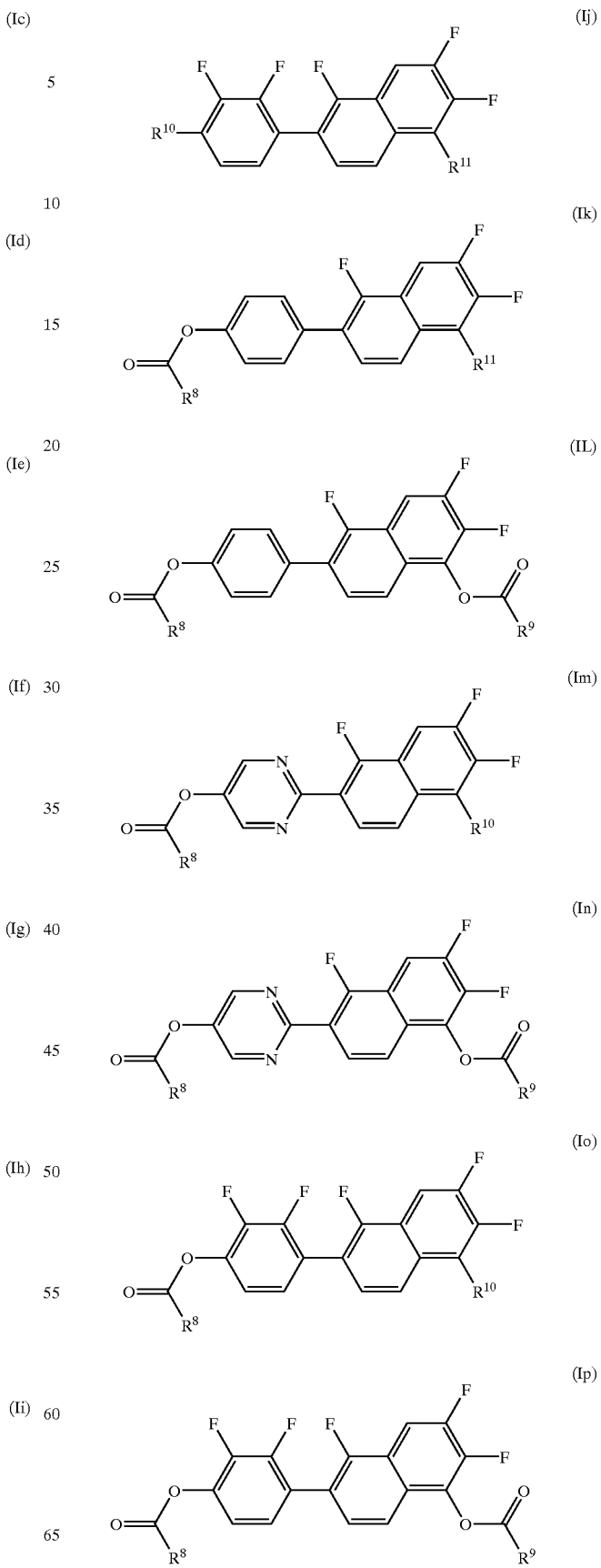

in which $R^8$ and $R^9$ are identical or different and are a straight-chained or branched alkyl chain having 1 to 19 carbon atoms, in which one or two hydrogen atoms may be replaced by F, and $R^{10}$ and $R^{11}$ are identical or different and are a straight-chain or branched alkyl or alkoxy chain having 1 to 20 or 1 to 19 carbon atoms respectively, in which one or two hydrogen atoms may be replaced by F, for 2,3-difluoronaphthalene derivatives selected from the following group (Ia) to (It):

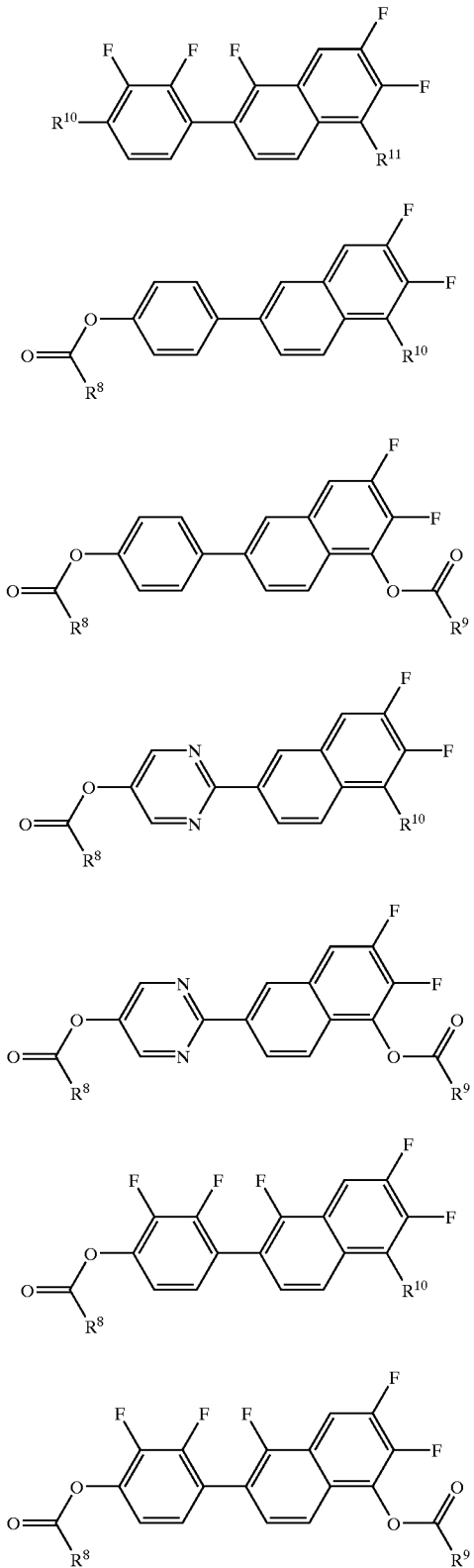

in which $R^8$ and $R^9$ are identical or different and are a straight-chain or branched alkyl chain having 1 to 19 carbon atoms, in which one or two hydrogen atoms may be replaced by F, and $R^{10}$ and $R^{11}$ are identical or different and are a straight-chain or branched alkyl or alkoxy chain having 1 to 20 or 1 to 19 carbon atoms respectively, in which one or two hydrogen atoms may be replaced by F.

5. A liquid-crystal mixture comprising one or more fluorinated naphthalene derivatives as claimed in claim 1.

6. A liquid-crystal mixture as claimed in claim 5, which is ferroelectric.

7. A liquid-crystal mixture as claimed in claim 5, which comprises from 0.01 to 80% by weight of one or more fluorinated naphthalene derivatives of the formula (I).

8. A ferroelectric switching and/or display device containing a ferroelectric liquid-crystal mixture as claimed in claim 6.

9. A ferroelectric switching and/or display device as claimed in claim 8, which is operated in $V_{min}$ mode.

* * * * *